(12) United States Patent
David et al.

(10) Patent No.: US 11,773,121 B2
(45) Date of Patent: Oct. 3, 2023

(54) ANTIVIRAL COMPOUNDS

(71) Applicant: VIROVAX LLC, Lawrence, KS (US)

(72) Inventors: Sunil Abraham David, Lawrence, KS (US); Naveen Kumar Rayala, Lawrence, KS (US)

(73) Assignee: VIROVAX LLC, Lawrence, KS (US)

( * ) Notice: Subject to any disclaimer, the term of this patent is extended or adjusted under 35 U.S.C. 154(b) by 36 days.

(21) Appl. No.: 17/157,733

(22) Filed: Jan. 25, 2021

(65) Prior Publication Data

US 2021/0238210 A1  Aug. 5, 2021

Related U.S. Application Data

(60) Provisional application No. 62/968,099, filed on Jan. 30, 2020.

(51) Int. Cl.
   *C07F 9/6561* (2006.01)
   *C07D 471/04* (2006.01)
   *A61P 31/14* (2006.01)

(52) U.S. Cl.
   CPC ............ *C07F 9/6561* (2013.01); *A61P 31/14* (2018.01); *C07D 471/04* (2013.01)

(58) Field of Classification Search
   None
   See application file for complete search history.

(56) References Cited

FOREIGN PATENT DOCUMENTS

WO    WO03068773    *  8/2003

OTHER PUBLICATIONS

Grant & Hackh's Chemical Dictionary (5th Ed. 1987) at p. 148.*

* cited by examiner

*Primary Examiner* — Po-Chih Chen
(74) *Attorney, Agent, or Firm* — MASCHOFF BRENNAN

(57) ABSTRACT

A compound can include the structure of Formula 1, derivative thereof, prodrug thereof, salt thereof, stereoisomer thereof, tautomer thereof, polymorph thereof, or solvate thereof, or having any chirality at any chiral center:

Formula 1

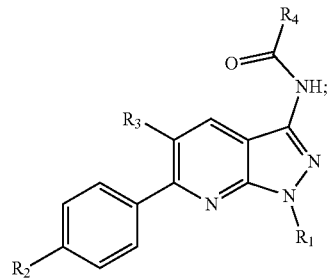

$R^1$ includes a hydrogen or a substituent; $R^2$ includes a hydroxyl, hydroxyl-forming prodrug, or hydroxyl-leaving chemical moiety; $R^3$ includes a halogen; and $R^4$ includes a heterocycle. The compound can be an antiviral compound used in antiviral therapies.

19 Claims, 4 Drawing Sheets

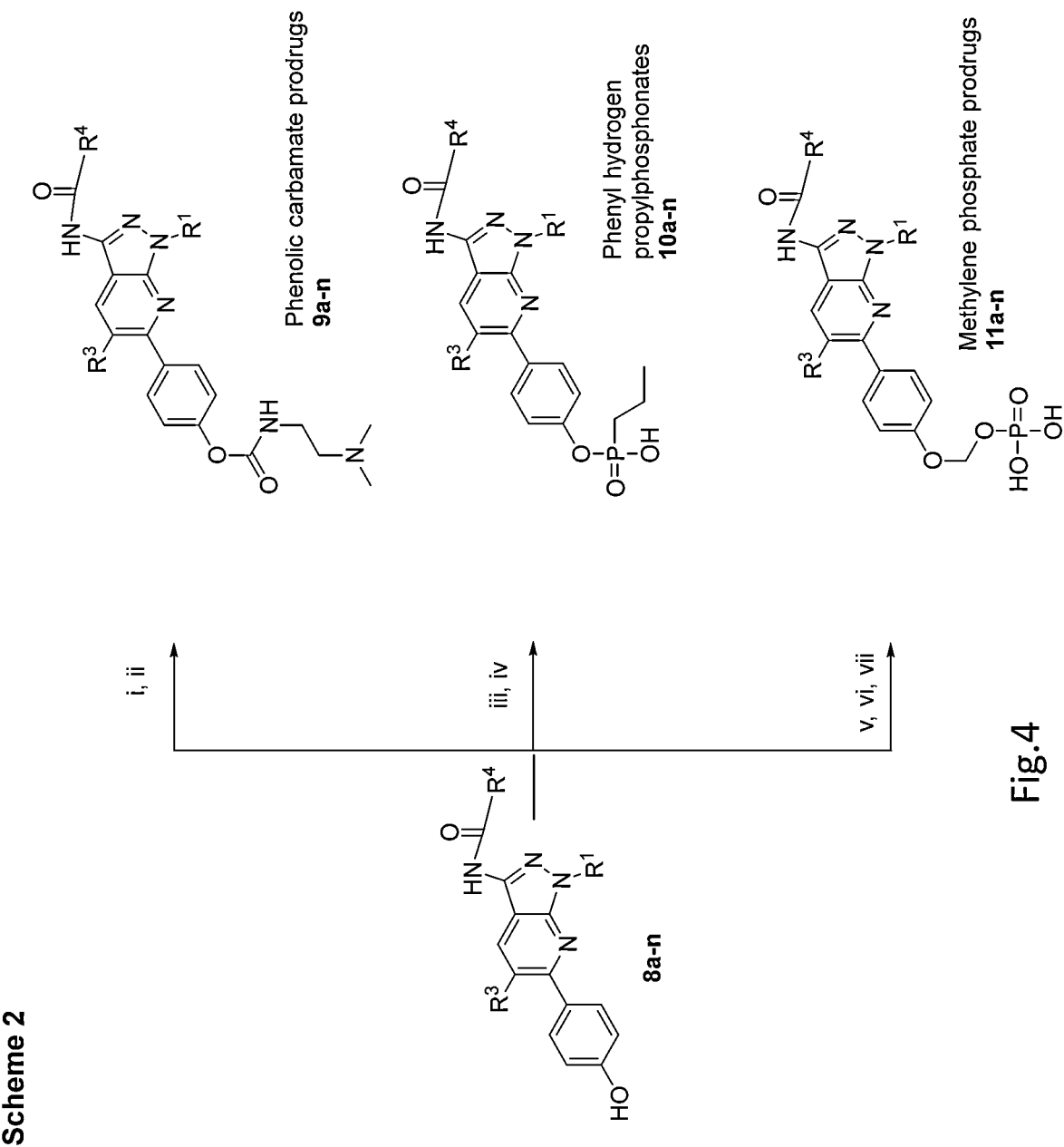

ANTIVIRAL COMPOUNDS

CROSS-REFERENCE TO RELATED APPLICATIONS

This patent application claims priority to U.S. Provisional Application No. 62/968,099 filed Jan. 30, 2020, which provisional is incorporated herein by specific reference in its entirety.

BACKGROUND

Field

The present disclosure relates to compounds for use in therapeutic methods for treating, preventing, or slowing progression of a viral related infection. More particularly, the present disclosure relates to antiviral compounds and pharmaceutical compositions thereof that can be used in the therapeutic methods for treating, preventing, or slowing progression of a viral infection from Chikungunya virus, Dengue virus (e.g., all four serotypes), Zika virus, Yellow Fever virus, and West Nile virus in a subject.

Description of Related Art

A viral infection often starts when enough viral particles are able to enter a host and begin replication without being neutralized by the host immune system. The viral particles have a life cycle that includes being generated by a host at an infection site, translocating to a new infection site whether in the same host or different host, entering a host cell, having its nucleic acid processed to case the host cell to produce a new copy of the viral particle, and the new viral particle escaping from its host cell on the journey to yet another infection site. Accordingly, viral research has looked at mechanisms for inhibiting any of these steps in order to provide immunizations, prophylactics, and treatments. However, many viruses do not have suitable therapeutics and no vaccines.

Chikungunya virus is transmitted via mosquito and does not have any vaccine to prevent infection or pharmaceutical to treat the infection. Similarly, Dengue virus also has no specific vaccination or pharmaceutical treatment. Zika virus, Yellow Fever virus and West Nile virus also have no specific antiviral treatment, where as in most viral infections the treatment is to manage the symptoms.

Thus, there is a need for a antiviral compounds that can be formulated into pharmaceutical compositions and used in therapeutic methods for viral infections, such as those described herein.

SUMMARY

In some embodiments, a compound can include the structure of Formula 1, derivative thereof, prodrug thereof, salt thereof, stereoisomer thereof, tautomer thereof, polymorph thereof, or solvate thereof, or having any chirality at any chiral center:

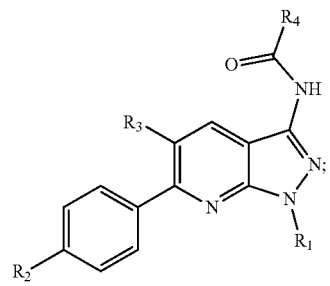

Formula 1 wherein: R includes a hydrogen or a substituent; $R^2$ includes a hydroxyl, hydroxyl-forming prodrug, or hydroxyl-leaving chemical moiety; $R^3$ includes a halogen; and $R^4$ includes a heterocycle. The compound can be an antiviral compound used in antiviral therapies.

In some embodiments, a pharmaceutical composition can include the antiviral compound and a pharmaceutically acceptable carrier.

In some embodiments, a method of synthesizing a compound can include: obtaining 6-(4-methoxyphenyl)-2-oxo-1,2-dihydropyridine-3-carbonitrile; reacting the 6-(4-methoxyphenyl)-2-oxo-1,2-dihydropyridine-3-carbonitrile with a halogenated succinimide to form the structure of Formula 2:

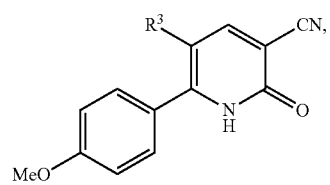

Formula 2 wherein $R^3$ is the halogen; reacting the compound of Formula 2 to form the compound of Formula 3:

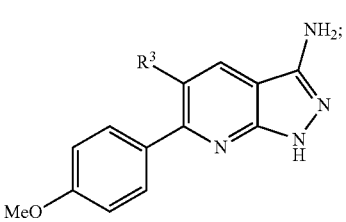

Formula 3 reacting the compound of Formula 3 to form the compound of Formula 4:

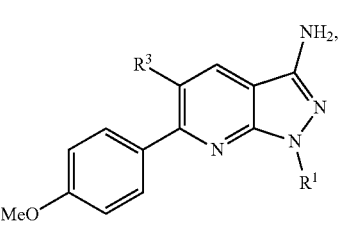

Formula 4 wherein R¹ is hydrogen or a substituent; reacting the compound of Formula 4 to form the compound of Formula 5:

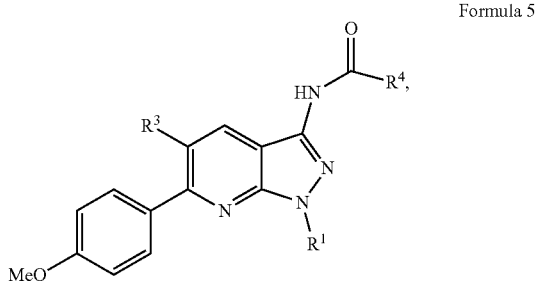

Formula 5 wherein R⁴ includes a heterocycle; and reacting the compound of Formula 5 to form the compound of Formula 6:

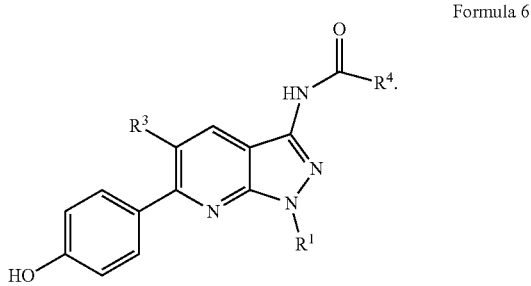

Formula 6

In some embodiments, a method of providing an antiviral therapy can include administering the compound of one of the embodiments to a subject having or suspected of having or exposed to a virus. In some aspects, the compound is administered to the subject in an effective amount for treating, inhibiting, preventing, or slowing progression of the virus. In some aspects, the virus is selected from: alpha viruses, including but not limited to, Chikungunya virus, and flaviviruses, including, but not limited to, Dengue virus, Zika virus, Yellow Fever Virus, West Nile Virus, Corona Virus, Flu Virus, or combinations thereof.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 4 includes an illustration of Scheme 2 for synthesizing prodrugs of the antiviral compounds.

Figure 1:
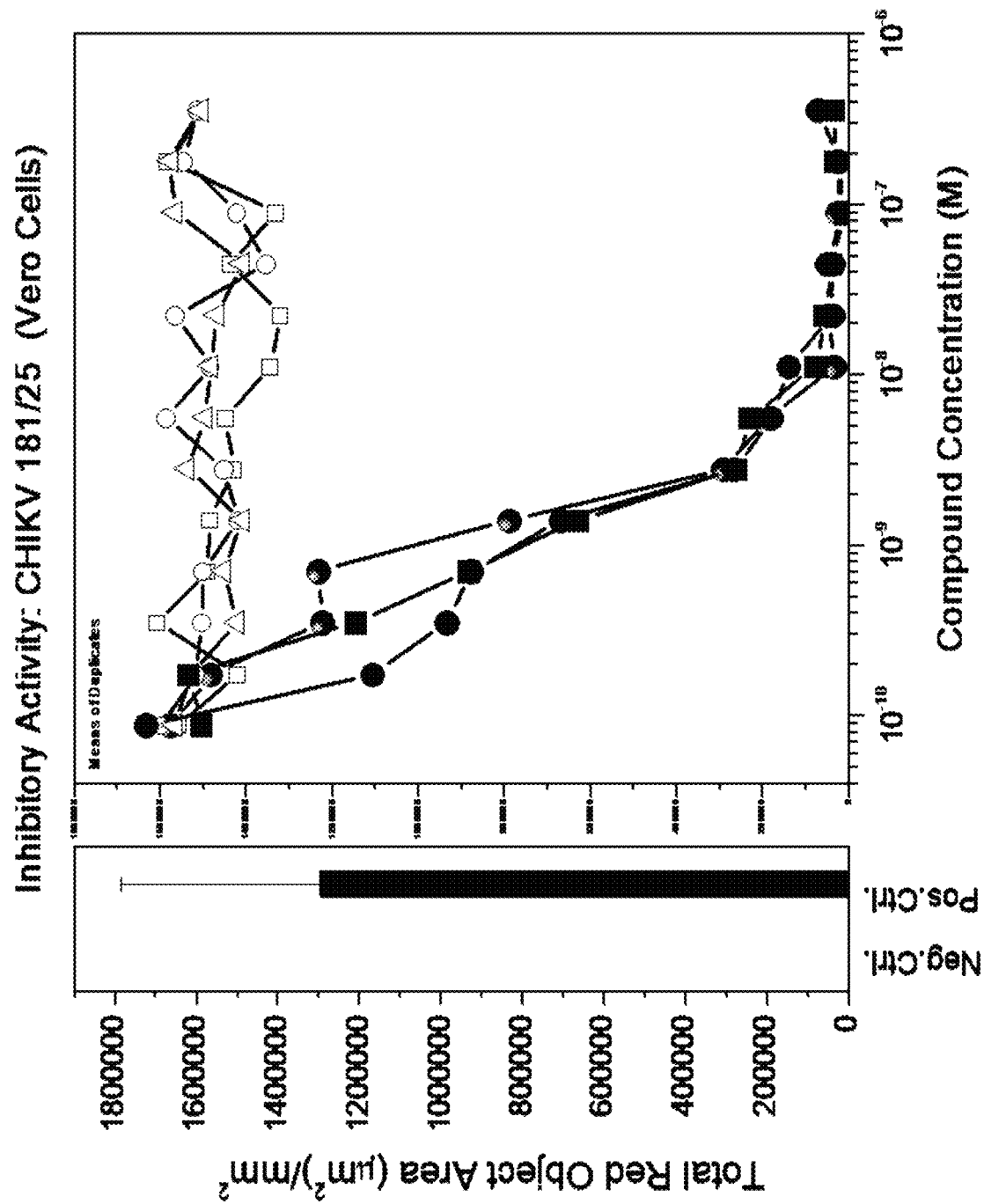
FIG. 1 includes a graph that shows the antiviral inhibitory activity of the compounds described herein for the Chikungunya Virus.

The elements and components in the figures can be arranged in accordance with at least one of the embodiments described herein, and which arrangement may be modified in accordance with the disclosure provided herein by one of ordinary skill in the art.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present technology includes compounds and/or materials for use as antiviral agents for a variety of viruses. The present disclosure relates to compounds for use in therapeutic methods for treating, preventing, or slowing progression of a viral related infection. More particularly, the present disclosure relates to antiviral compounds and pharmaceutical compositions thereof that can be used in the therapeutic methods for treating, preventing, or slowing progression of a viral infection from Chikungunya virus, Dengue virus (e.g., all four serotypes), Zika virus, Yellow Fever Virus, and West Nile Virus in a subject.

A compound collection was screened for antiviral effects, which yielded hits. A structure-activity relationship study of the hits identified 120 congeners that possess antiviral effects against a wide range of viruses, including, but not limited to, Corona Virus, Chikungunya virus, Dengue virus (all four serotypes), Zika virus, Yellow Fever Virus, and West Nile Virus. Additionally, the compounds can be used for screening against any virus, and then those with activity can be identified and used as an antiviral for one or more different viruses.

In some embodiments, an antiviral pharmaceutical composition can include a compound that functions as an antiviral agent. Such a compound can include the core scaffold structure of Formula 1, which may or may not be substituted. The antiviral compound can include a structure under Formula 1 derivative thereof, prodrug thereof, salt thereof, stereoisomer thereof, tautomer thereof, polymorph thereof, or solvate thereof, or having any chirality at any chiral center,

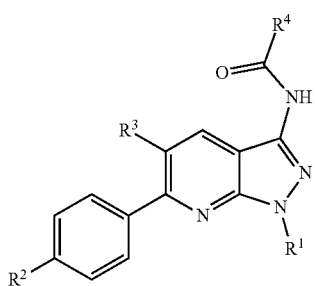

Formula 1

The structure of Formula 1 can include hydrogen or any substituent R group for $R^1$, $R^2$, $R^3$, and/or $R^4$, such as those described herein or otherwise known.

In some embodiments, the substituent R group (e.g., chemical moiety) for $R^1$, $R^2$, $R^3$, and/or $R^4$ are independently a hydrogen, halogens, hydroxyls, alkoxys, straight aliphatics, branched aliphatics, cyclic aliphatics, substituted aliphatics, unsubstituted aliphatics, saturated aliphatics, unsaturated aliphatics, aromatics, polyaromatics, substituted aromatics, hetero-aromatics, hetero-polyaromatics, substituted hetero-polyaromatics, amines, primary amines, secondary amines, tertiary amines, aliphatic amines, carbonyls, carboxyls, amides, esters, phosphates, alkyl phosphates, phosphonate, alkyl phosphonate, carbamates, alkyl carbamates, amino alkyl carbamates, amino acid carbamates, amino acids, peptides, polypeptides, derivatives thereof, substituted or unsubstituted, or combinations thereof as well as other well-known chemical substituents In some embodiments, the substituent R group (e.g., chemical moiety) for $R^1$, $R^2$, $R^3$, and/or $R^4$ are independently hydrogen, alkyl, alkenyl, alkynyl, aryl, polyaryl, hetroaryl, polyhetroaryl, alkaryl, aralkyl, halo, hydroxyl, sulfhydryl, alkoxy, alkenyloxy, alkynyloxy, aryloxy, acyl, alkylcarbonyl, arylcarbonyl, acyloxy, alkoxycarbonyl, aryloxycarbonyl, halocarbonyl, alkylcarbonato, arylcarbonato, carboxy, carboxylato, carbamoyl, mono-(alkyl)-substituted carbamoyl, di-(alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-(alkyl)-substituted amino, mono- and di-(aryl)-substituted amino, alkylamido arylamido, imino, alkylimino, arylimino, nitro, nitroso, sulfo, sulfonato, alkylsulfanyl, arylsulfanyl, alkylsulfinyl, arylsulfinyl, alkylsulfonyl, arylsulfonyl, phosphono, phosphonato, phosphinato, phospho, phosphino, any with or without hetero atoms, derivatives thereof, and combinations thereof.

In some embodiments, the substituent R group (e.g., chemical moiety) for R, $R^2$, $R^3$, and/or $R^4$ are can be independently any one or more of the substituents selected from the group of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), di-substituted arylcarbamoyl (—(CO)—NH-aryl)$_2$, thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-substituted arylthiocarbamoyl (—(CS)—NH-aryl), di-substituted arylthiocarbamoyl (—(CS)—NH-aryl)$_2$, carbamido (—NH—(CO)—NH$_2$), mono-($C_1$-$C_{24}$ alkyl)-substituted carbamido (—NH—(CO)—NH($C_1$-$C_{24}$ alkyl)), di-($C_1$-$C_{24}$ alkyl)-substituted carbamido (—NH—(CO)—N($C_1$-$C_{24}$ alkyl)$_2$), mono-substituted aryl carbamido (—NH—(CO)—NH-aryl), di-substituted aryl carbamido (—NH—(CO)—N-(aryl)$_2$), carbamate (—O—(CO)—NH—), alkyl carbamate (—O—(CO)—NH-alkyl), cyano (—C≡N), isocyano (—N$^+$≡C$^-$), cyanato (—O—C≡N), isocyanato (—O—N$^+$≡C$^-$), thiocyanato (—S—C≡N), isothiocyanato (—S—N$^+$≡C$^-$), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_6$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, $C_1$-$C_{24}$ alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfonic acid (—SO$_2$—OH), sulfonato (—SO$_2$—O—)—$C_1$-$C_{24}$ alkylsulfanyl (—S— alkyl; also termed "alkylthio"), $C_5$-$C_{20}$ arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O—)), phospho (—PO$_2$), phosphino (—PH$_2$), phosphate, phosphonate, alkyl phosphonate, sulphate, any with or without hetero atoms (e.g., N, O, P, S, or other) where the hetero atoms can be substituted (e.g., hetero atom substituted for carbon in chain or ring) for the carbons or in addition thereto (e.g., hetero atom added to carbon chain or ring) swapped, any including straight chains, any including branches, and any inducing rings, derivatives thereof, and combinations thereof.

In some embodiments, the substituent R group (e.g., chemical moiety) for R, $R^2$, $R^3$, and/or $R^4$ are can be any ring structure with a single ring or two or more fused rings, which can be cycloaliphatic, hetero cycloaliphatic, aryl, hetero aryl, polyaryl, poly hetero aryl, or combinations thereof with 4, 5, 6, 7, 8, 9, 10, 11, or 12 atoms per ring.

In some embodiments of Formula 1, the R groups can be defined as follows. The $R^1$ can include a straight alkyl, branched alkyl, cyclic alkyl, or combination thereof, which can be substituted or unsubstituted. The $R^2$ can include a hydroxyl, alcohol, phosphate, alkylphosphate, phosphonate, alkyl phosphonate, carbamate, alkylcarbamate, amino alkylcarbamate, or others, which can be substituted or unsubstituted. The $R^3$ can include a halogen, such as F, Cl, Br, and I. The $R^4$ can include a 5, 6, or 7 membered aromatic ring (aryl), which may or may not include hetero atoms, such as 0, S or N, and which can be substituted or unsubstituted.

In some embodiments of Formula 1, the $R^1$ can include a $C_1$-$C_{24}$ alkyl, $C_4$-$C_{24}$ branched alkyl, or $C_4$-$C_{24}$ alkylcycloalkyl. In some embodiments, of Formula 1, the $R^1$ can include $C_1$-$C_{12}$ alkyl, $C_4$-$C_{12}$ branched alkyl, or $C_4$-$C_{12}$ alkylcycloalkyl. In some embodiments, of Formula 1, the $R^1$ can include $C_1$-$C_8$ alkyl, $C_4$-$C_8$ branched alkyl, or $C_4$-$C_8$ alkylcycloalkyl.

In some embodiments of Formula 1, the $R^2$ can include a hydroxl, an alkoxy phosphate, an alkyl phosphonate, or an amino alkyl carbamate. In some embodiments of Formula 1, the $R^2$ can include a hydroxl, a $C_1$-$C_4$ alkoxy phosphate, a $C_1$-$C_8$ alkyl phosphonate, or an amino $C_1$-$C_8$ alkyl carbamate.

In some embodiments of Formula 1, the $R^3$ can include I, Cl, or Br.

In some embodiments of Formula 1, the $R^4$ can include a 5 or 6 membered hetero aromatic ring (aryl) with at least one hetero atom of O, N, or S. In some aspects, the $R^4$ can include a pyrrolyl, furanyl, thiophenyl, imidazolyl, pyrazolyl, oxathiolyl, isoxathiolyl, thiazolyl, isothiazolyl, triazolyl, furazanyl, oxadiozolyl, thiadizolyl, dioxazolyl, dithiazolyl, tetrazolyl, oxatetrazolyl, thiatetrazolyl, pentazolyl, pyridinyl, pyranyl, thiopyranyl, diazinyl, oxazinyl, thiazinyl, dioxinyl, dithiinyl, triazinyl, tetrazinyl, pentazinyl, azepinyl, oxepinyl, thiepinyl, diazepinyl, or thiazepinyl.

In some embodiments of Formula 1, the R groups can be defined as follows. In some embodiments of Formula 1, the $R^1$ can be hexyl, isohexyl, heptyl, isoheptyl, ω-cyclopropyl-propyl, or ω-cyclopropyl-butyl. In some embodiments of Formula 1, the $R^2$ can be —OH, —O—$CH_2$—$PO_4H_2$ and salts thereof, —O(CO)$NH_2C_2H_4$N(Me)$_2$ and salts thereof, —O(CO)$NH_2C_3H_6$N(Me)$_2$ and salts thereof; or —O(PO$_2$H)$CH_2CH_2CH_3$. In some embodiments of Formula 1, $R^3$ can be Br or Cl. In some embodiments of Formula 1, $R^4$ can be is a pyridine, thiazole, or isothiazole. In some embodiments of Formula 1, the $R^4$ can be a pyridine, such as 3-pyridinyl (e.g., nicotinyl), or an isothiazole, such as 3-isothiazolyl. For the pyridine, the nitrogen can be in the para, meta, or ortho position, where the meta position is preferred. For the isothiazole, the N and S can be adjacent with a carbon between the N and the carbon having the bond to the amide and a carbon between the S and the carbon having the bond to the amide.

In some embodiments, the antiviral compounds can be nicotinamide derivatives (e.g., pyridine as $R^4$) or isothiazole or other thiazole derivatives at the $R^4$ substituent location.

Nicotinamide Derivatives

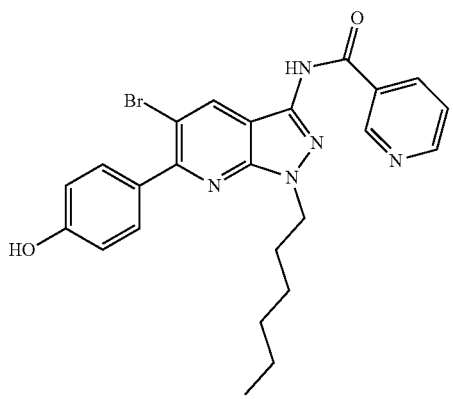

N-(5-bromo-1-hexyl-6-(4-hydroxyphenyl)-1H-pyrazolo[3,4-b]pyridin-3-yl)nicotinamide

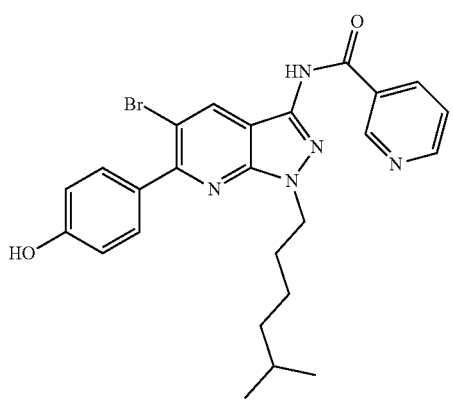

N-(5-bromo-6-(4-hydroxyphenyl)-1-(5-methylhexyl)-1H-pyrazolo[3,4-b]pyridin-3-yl)nicotinamide

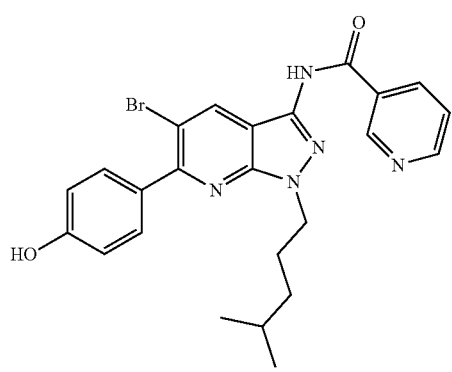

N-(5-bromo-6-(4-hydroxyphenyl)-1-(4-methylpentyl)-1H-pyrazolo[3,4-b]pyridin-3-yl)nicotinamide

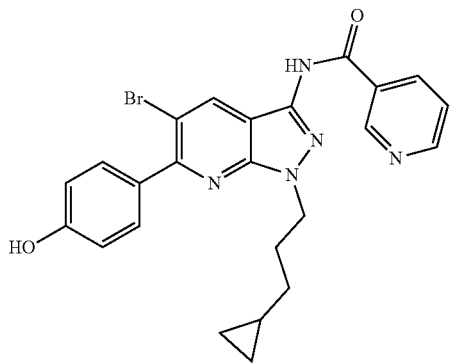

N-(5-bromo-1-(3-cyclopropylpropyl)-6-(4-hydroxyphenyl)-1H-pyrazolo[3,4-b]pyridin-3-yl)nicotinamide -continued

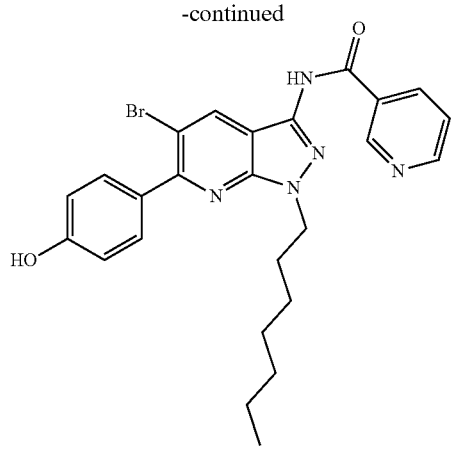

N-(5-bromo-1-hepyl-6-(4-hydroxyphenyl)-1H-pyrazolo[3,4-b]
pyridin-3-yl)nicotinamide

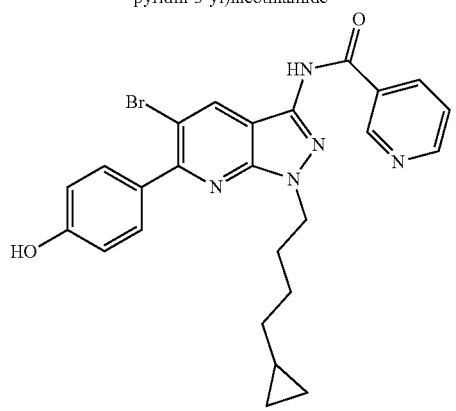

N-(5-bromo-1-(4-cyclopropylbutyl)-6-(4-hydroxyphenyl)-1H-
pyrazolo[3,4-b]pyridin-3-yl)nicotinamide

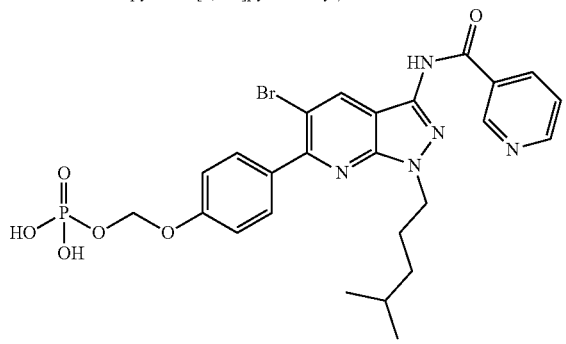

(4-(5-bromo-1-(4-methylpentyl)-3-(nicotinamido)-1H-pyrazolo[3,4-b]
pyridin-6-yl)phenoxy)methyl dihydrogen phosphate

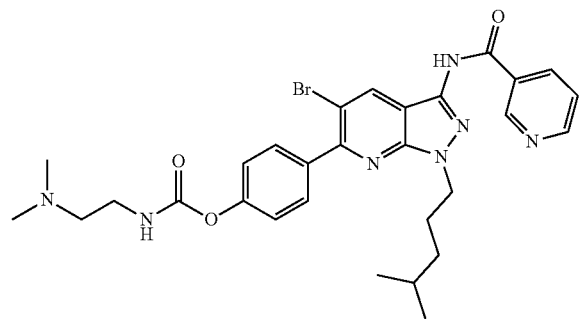

4-(5-bromo-1-(4-methylpentyl)-3-(nicotinamido)-1H-pyrazolo[3,4-b]
pyridin-6-yl)phenyl (2-(dimethylamino)ethyl)carbamate -continued

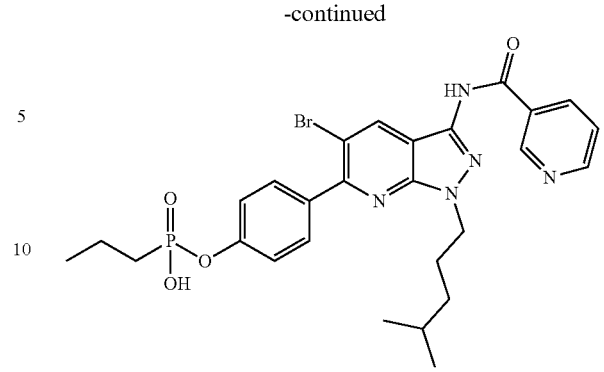

4-(5-bromo-1-(4-methylpentyl)-3-(nicotinamido)-1H-pyrazolo[3,4-b]
pyridin-6-yl)phenyl hydrogen propylphosphonate

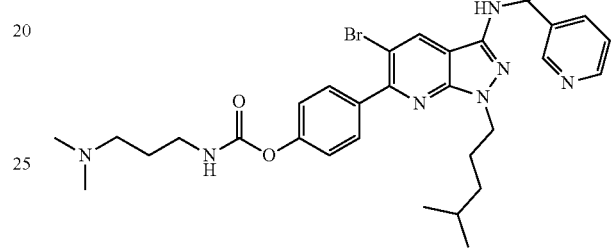

4-(5-bromo-1-(4-methylpentyl)-3-(nicotinamido)-1H-pyrazolo[3,4-b]
pyridin-6-yl)phenyl (3-(dimethylamino)propyl)carbamate

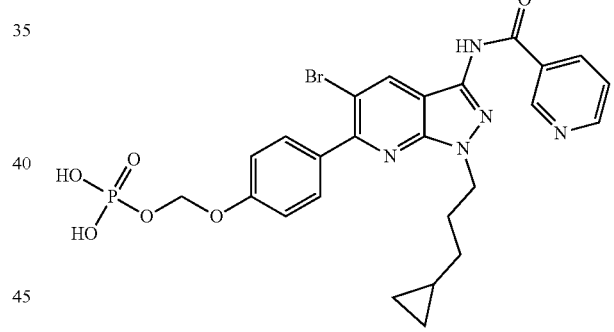

(4-(5-bromo-1-(3-cyclopropylpropyl)-3-(nicotinamido)-1H-
pyrazolo[3,4-b]pyridin-6-yl)phenoxy)methyl dihydrogen phosphate

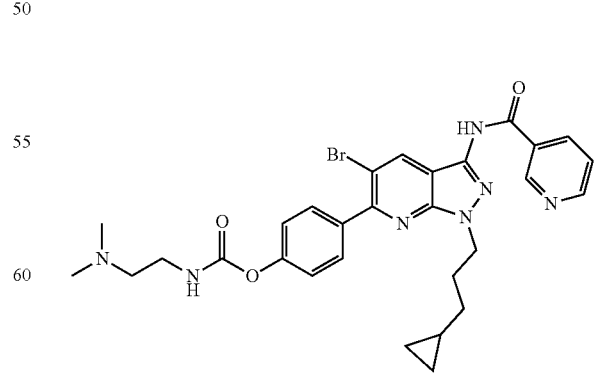

4-(5-bromo-1-(3-cyclopropylpropyl)-3-(nicotinamido)-1H-pyrazolo[3,4-b]
pyridin-6-yl)phenyl (2-(dimethylamino)ethyl)carbamate -continued

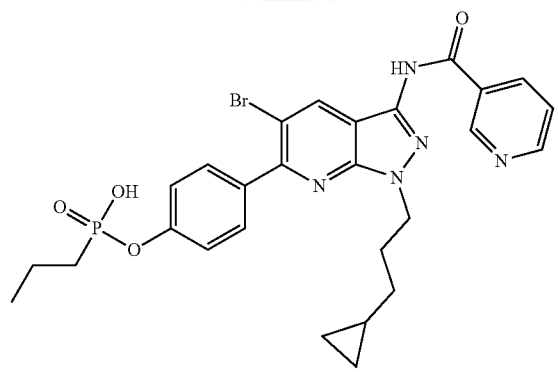

4-(5-bromo-1-(3-cyclopropylpropyl)-3-(nicotinamido)-1H-pyrazolo[3,4-b]pyridin-6-yl)phenyl hydrogen propylphosphonate

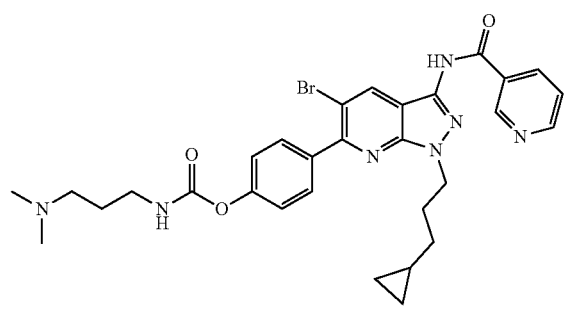

4-(5-bromo-1-(3-cyclopropylpropyl)-3-(nicotinamido)-1H-pyrazolo[3,4-b]pyridin-6-yl)phenyl 3-(dimethylamino)propyl)carbamate

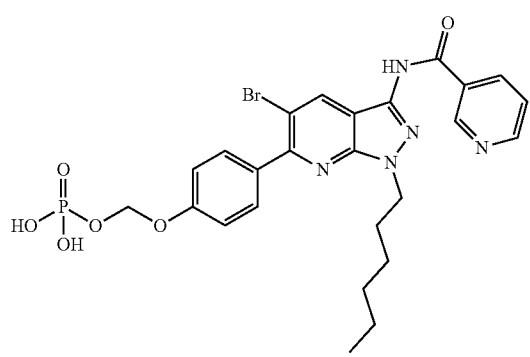

(4-(5-bromo-1-hexyl-3-(nicotinamido)-1H-pyrazolo[3,4-b]pyridin-6-yl)phenoxy)methyl dihydrogen phosphate

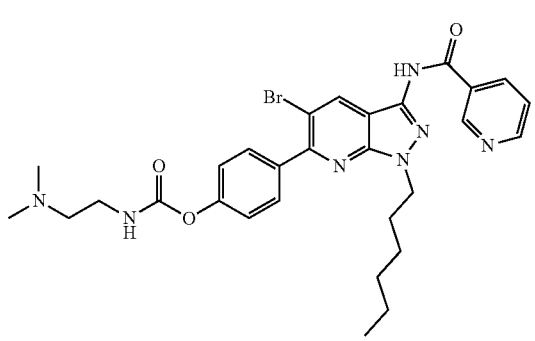

4-(5-bromo-1-hexyl-3-(nicotinamido)-1H-pyrazolo[3,4-b]pyridin-6-yl)phenyl (2-(dimethylamino)ethyl)carbamate -continued

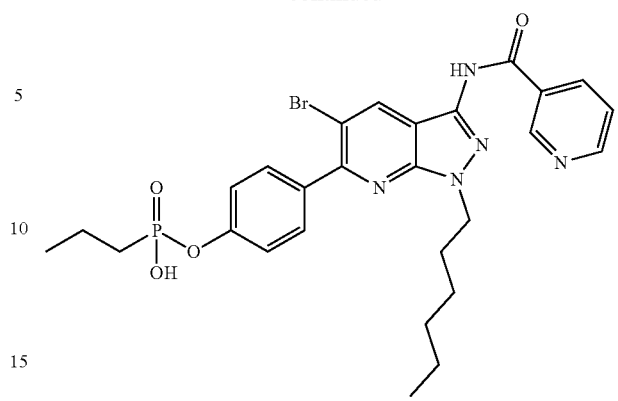

4-(5-bromo-1-hexyl-3-(nicotinamido)-1H-pyrazolo[3,4-b]pyridin-6-yl)phenyl hydrogen propylphosphonate

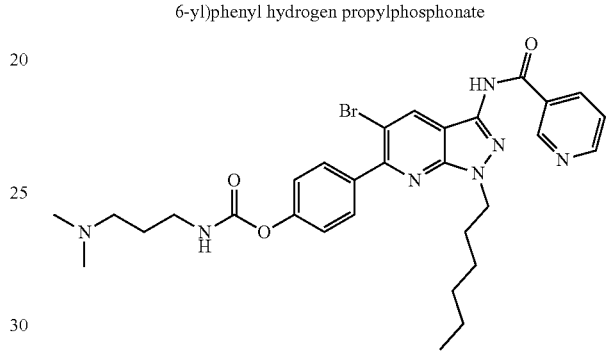

4-(5-bromo-1-hexyl-3-(nicotinamido)-1H-pyrazolo[3,4-b]pyridin-6-yl)phenyl (3-dimethylamino)propyl)carbamate

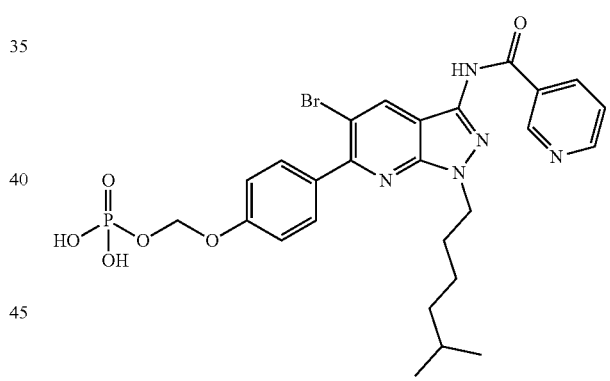

(4-(5-bromo-1-(5-methylhexyl)-3-(nicotinamido)-1H-pyrazolo[3,4-b]pyridin-6-yl)phenoxy)methyl dihydrogen phosphate

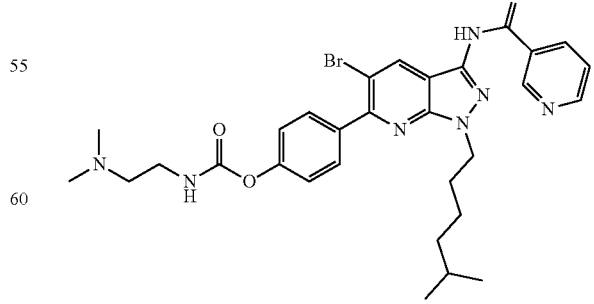

4-(5-bromo-1-(5-methylhexyl)-3-(nicotinamido)-1H-pyrazolo[3,4-b]pyridin-6-yl)phenyl (2-(dimethylamino)ethyl)carbamate

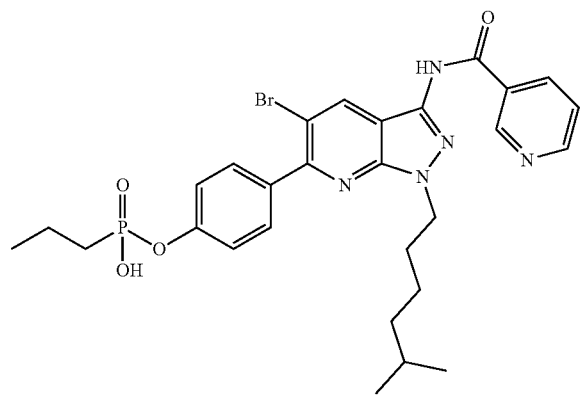

4-(5-bromo-1-(5-methylhexyl)-3-(nicotinamido)-1H-pyrazolo
[3,4-b]pyridin-6-yl)phenyl hydrogen propylphosphonate

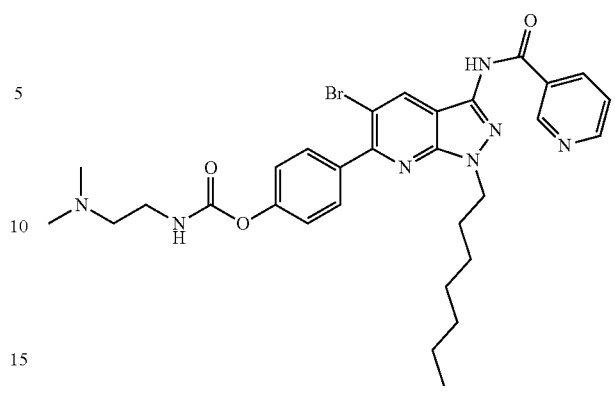

4-(5-bromo-1-heptyl-3-(nicotinamido)-1H-pyrazolo[3,4-b]pyridin-
6-yl)phenyl (2-(dimethylamino)ethyl)carbamate

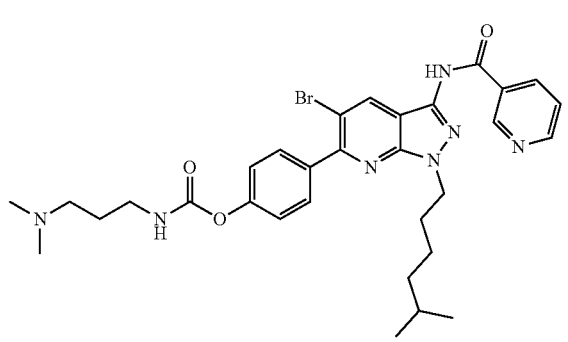

4-(5-bromo-1-(5-methylhexyl)-3-(nicotinamido)-1H-pyrazolo
[3,4-b]pyridin-6-yl)phenyl (3-(dimethylamino)propyl)carbamate

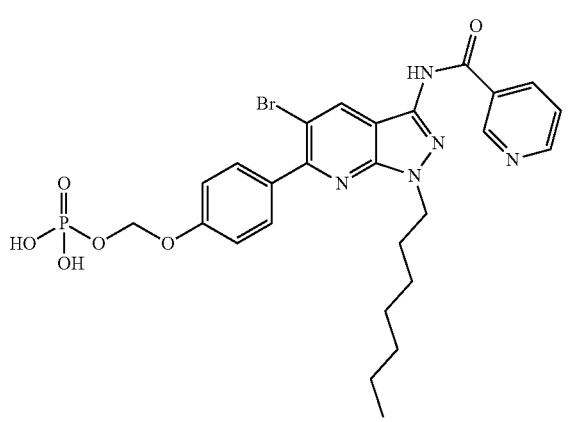

(4-5-bromo-1-heptyl-3-(nicotinamido)-1H-pyrazolo[3,4-b]pyridin-
6-yl)phenoxy)methyl dihydrogen phosphate

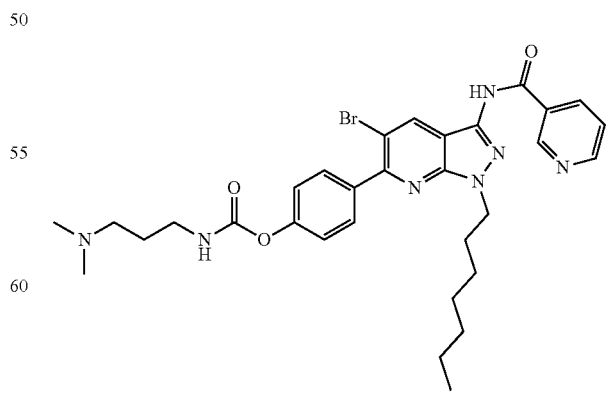

4-(5-bromo-1-heptyl-3-(nicotinamido)-1H-pyrazolo[3,4-b]pyridin-
6-yl)phenyl hydrogen propylphosphonate 4-(5-bromo-1-heptyl-3-(nicotinamido)-1H-pyrazolo[3,4-b]pyridin-
6-yl)phenyl (3-dimethylamino)propyl)carbamate -continued

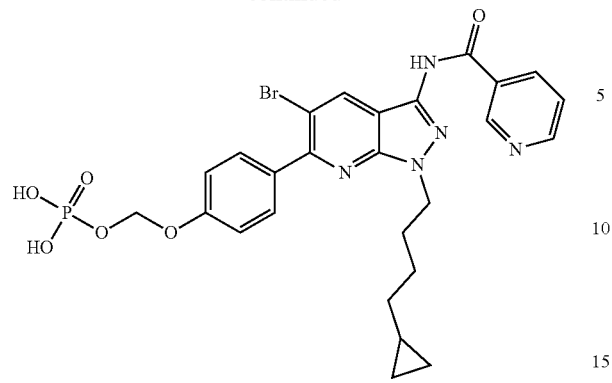

(4-(5-bromo-1-(4-cyclopropylbutyl)-3-(nicotinamido)-1H-pyrazolo[3,4-b]
pyridin-6-yl)phenoxy)methyl dihydrogen phosphate

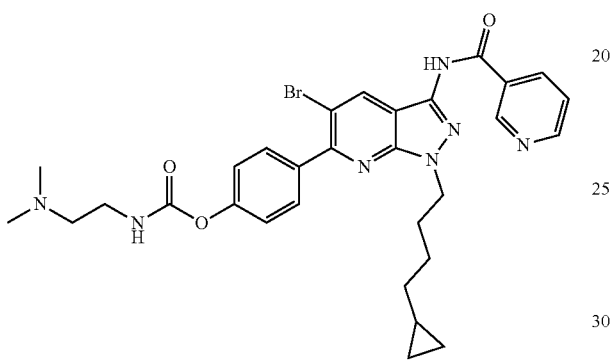

4-(5-bromo-1-(4-cyclopropylbutyl)-3-(nicotinamido)-1H-pyrazolo[3,4-b]
pyridin-6-yl)phenyl (2-(dimethylamino)ethyl)carbamate

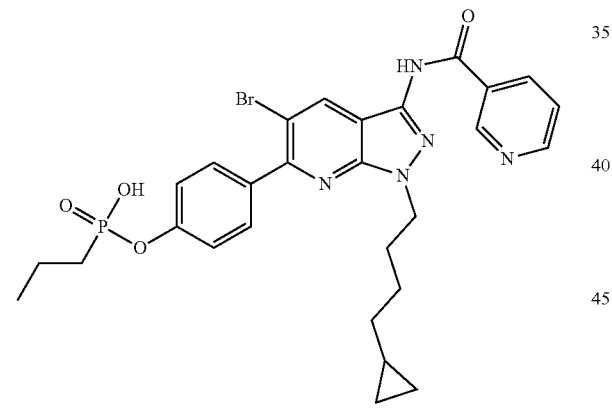

4-(5-bromo-1-(4-cyclopropylbutyl)-3-(nicotinamido)-1H-pyrazolo
[3,4-b]pyridin-6-yl)phenyl hydrogen propylphosphonate

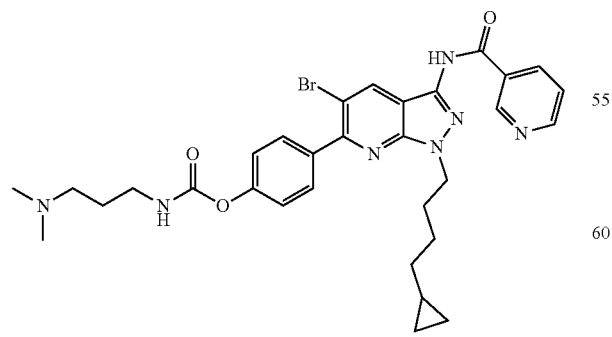

4-(5-bromo-1-(4-cyclopropylbutyl)-3-(nicotinamido)-1H-pyrazolo
[3,4-b]pyridin-6-yl)phenyl (3-(dimethylamino)propyl)carbamate -continued

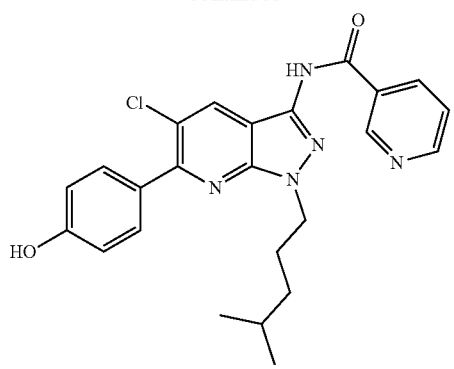

N-(5-chloro-6-(4-hydroxyphenyl)-1-(4-methylpentyl)-1H-
pyrazolo[3,4-b]pyridin-3-yl)nicotinamide

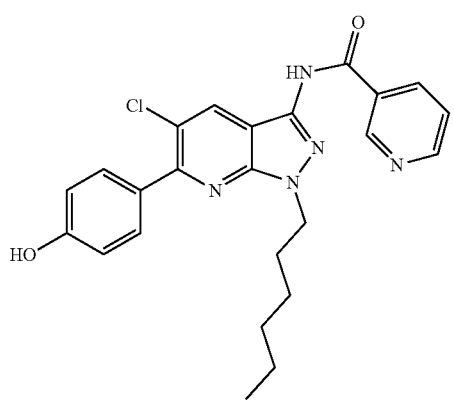

N-(5-chloro-1-hexyl-6-(4-hydroxyphenyl)-1H-pyrazolo
[3,4-b]pyridin-3-yl)nicotinamide

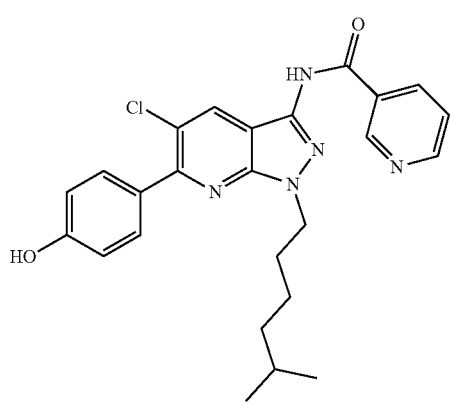

N-(5-chloro-6-(4-hydroxyphenyl)-1-(5-methylhexyl)-1H-
pyrazolo[3,4-b]pyridin-3-yl)nicotinamide

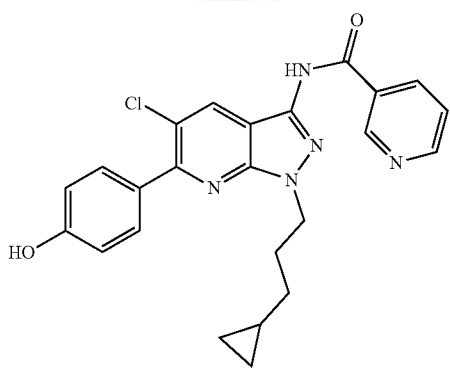

N-(5-chloro-1-(3-cyclopropylpropyl)-6-(4-hydroxyphenyl)-
1H-pyrazolo[3,4-b]pyridin-3-yl)nicotinamide

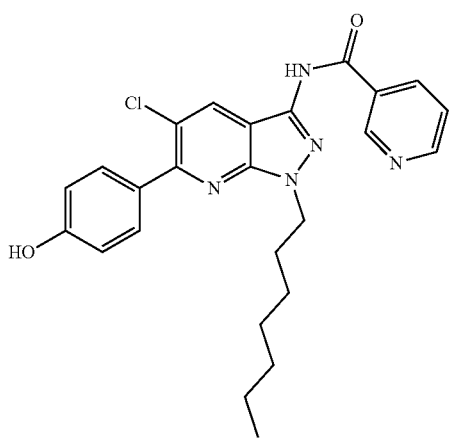

N-(5-chloro-1-heptyl-6-(4-hydroxyphenyl)-1H-
pyrazolo[3,4-b]pyridin-3-yl)nicotinamide

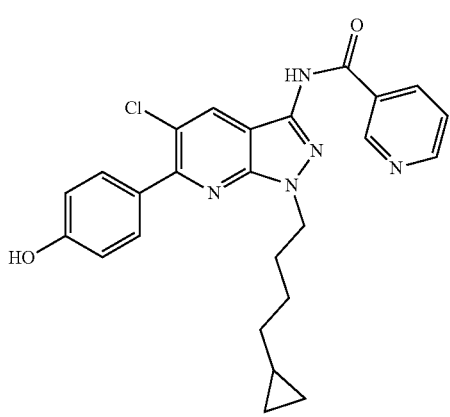

N-(5-chloro-1-(4-cyclopropylbutyl)-6-(4-hydroxyphenyl)-1H-
pyrazolo[3,4-b]pyridin-3-yl)nicotinamide

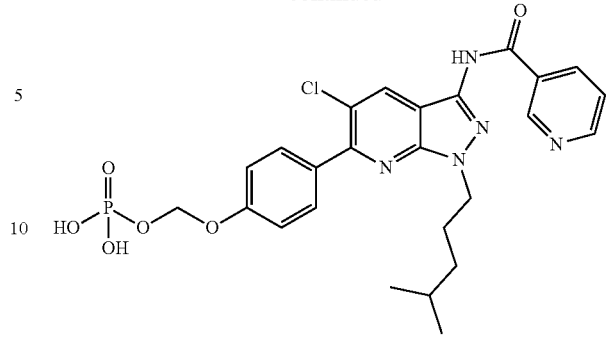

(4-(5-chloro-1-(4-methylpentyl)-3-(nicotinamido)-1H-pyrazolo[3,4-b]
pyridin-6-yl)phenoxy)methyl dihydrogen phosphate

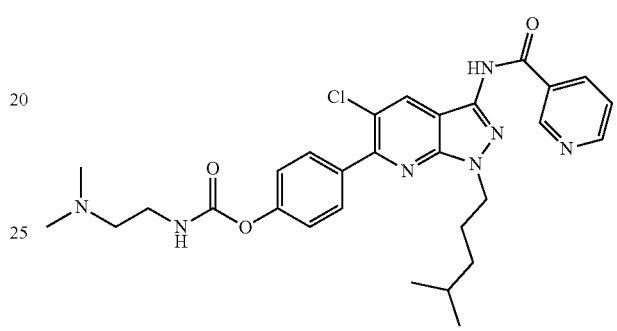

4-(5-chloro-1-(4-methylpentyl)-3-(nicotinamido)-1H-pyrazolo[3,4-b]
pyridin-6-yl)phenyl (2-(dimethylamino)ethyl)carbamate

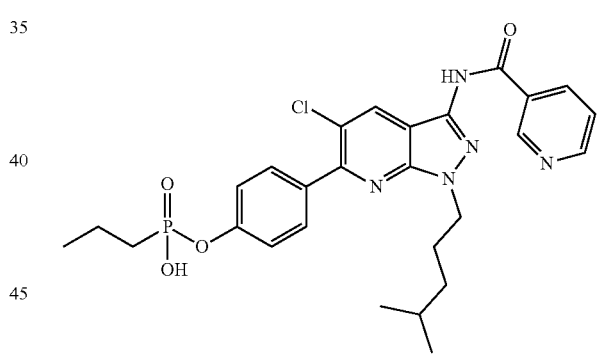

4-(5-chloro-1-(4-methylpentyl)-3-(nicotinamido)-1H-pyrazolo[3,4-b]
pyridin-6-yl)phenyl hydrogen propylphosphonate

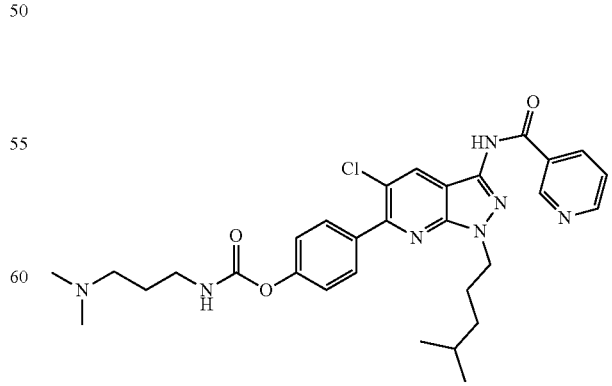

4-(5-chloro-1-(4-methylpentyl)-3-(nicotinamido)-1H-pyrazolo[3,4-b]
pyridin-6-yl)phenyl (3-(dimethylamino)propyl)carbamate

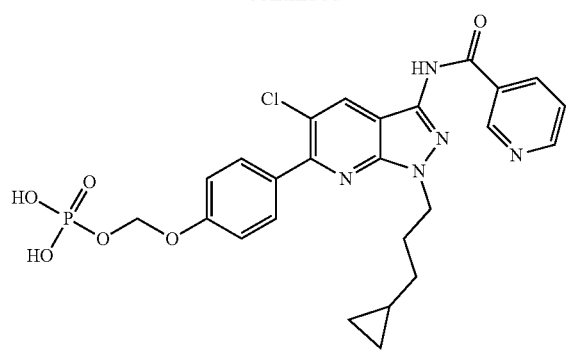

(4-(5-chloro-1-(3-cyclopropylpropyl)-3-(nicotinamido)-1H-pyrazolo[3,4-b]pyridin-6-yl)phenoxy)methyl dihydrogen phosphate

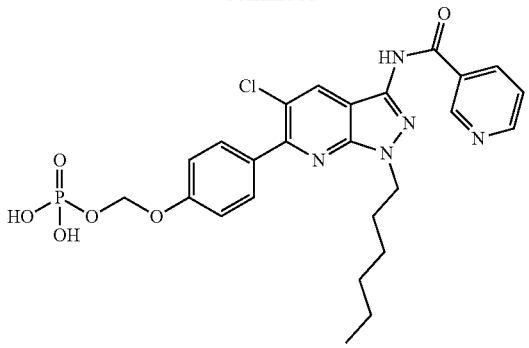

(4-(5-chloro-1-hexyl-3-(nicotinamido)-1H-pyrazolo[3,4-b]pyridin-6-yl)phenoxy)methyl dihydrogen phosphate

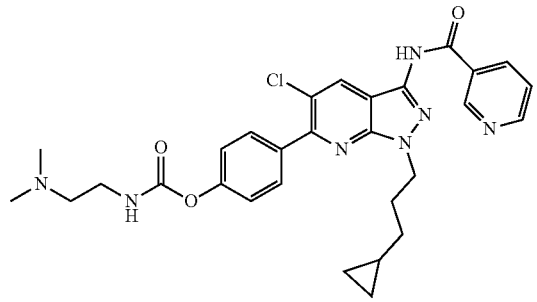

4-(5-chloro-1-(3-cyclopropylpropyl)-3-(nicotinamido)-1H-pyrazolo[3,4-b]pyridin-6-yl)phenyl (2-(dimethylamino)ethyl)carbamate

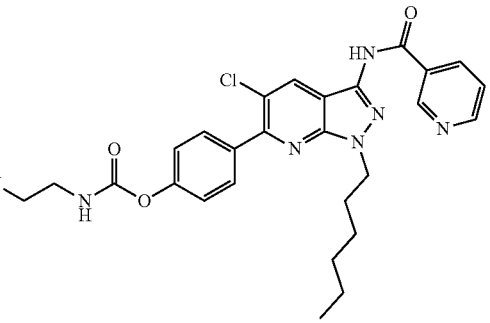

4-(5-chloro-1-hexyl-3-(nicotinamido)-1H-pyrazolo[3,4-b]pyridin-6-yl)phenyl (2-(dimethylamino)ethyl)carbamate

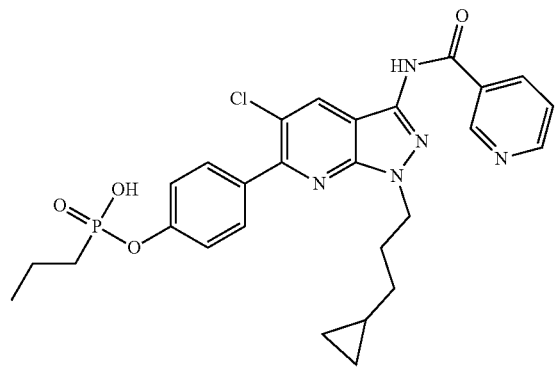

4-(5-chloro-1-(3-cyclopropylpropyl)-3-(nicotinamido)-1H-pyrazolo[3,4-b]pyridin-6-yl)phenyl hydrogen propylphosphonate

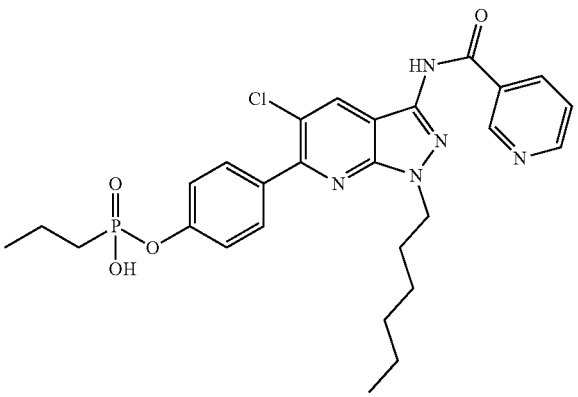

4-(5-chloro-1-hexyl-3-(nicotinamido)-1H-pyrazolo[3,4-b]pyridin-6-yl)phenyl hydrogen propylphosphonate

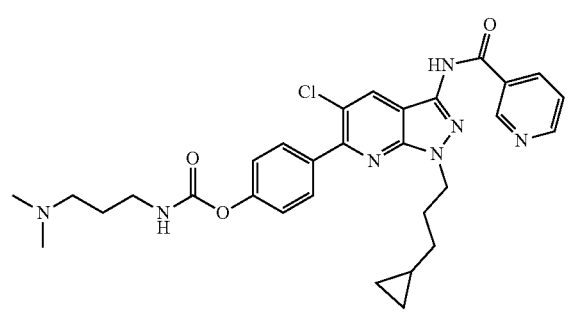

4-(5-chloro-1-(3-cyclopropylpropyl)-3-(nicotinamido)-1H-pyrazolo[3,4-b]pyridin-6-yl)phenyl (3-(dimethylamino)propyl)carbamate

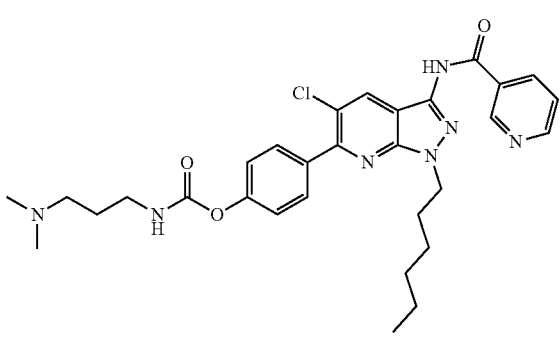

4-(5-chloro-1-hexyl-3-(nicotinamido)-1H-pyrazolo[3,4-b]pyridin-6-yl)phenyl (3-(dimethylamino)propyl)carbamate 21
-continued

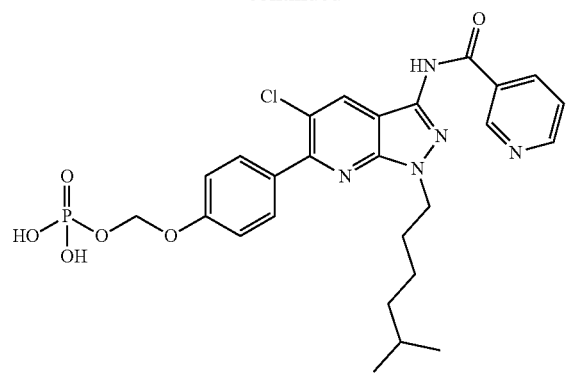

(4-(5-chloro-1-(5-methylhexyl)-3-(nicotinamido)-1H-pyrazolo[3,4-b]
pyridin-6-yl)phenoxy)methyl dihydrogen phosphate

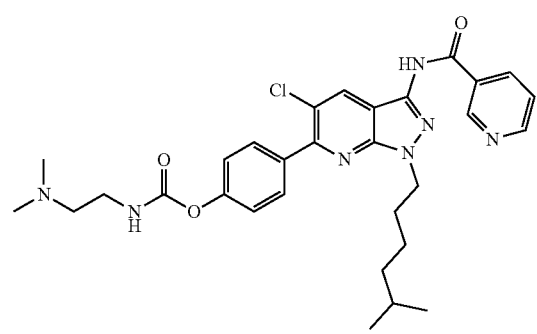

4-(5-chloro-1-(5-methylhexyl)-3-(nicotinamido)-1H-pyrazolo
[3,4-b]pyridin-6-yl)phenyl (2-(dimethylamino)ethyl)carbamate

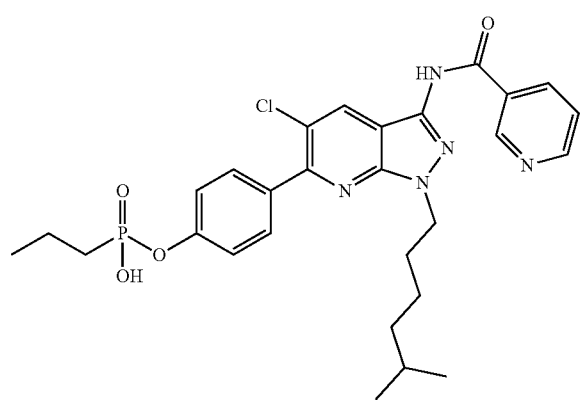

4-(5-chloro-1-(5-methylhexyl)-3-(nicotinamido)-1H-pyrazolo
[3,4-b]pyridin-6-yl)phenyl hydrogen propylphosphonate

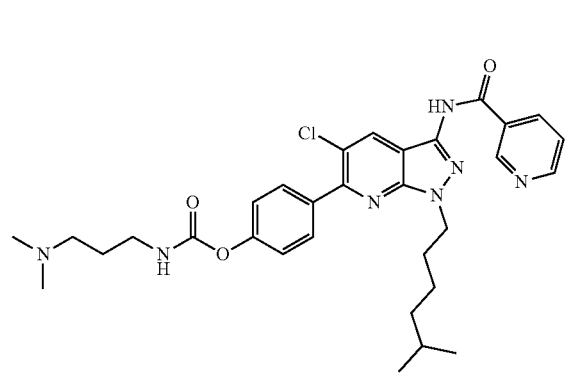

4-(5-chloro-1-(5-methylhexyl)-3-(nicotinamido)-1H-pyrazolo
[3,4-b]pyridin-6-yl)phenyl (3-(dimethylamino)propyl)carbamate 22
-continued

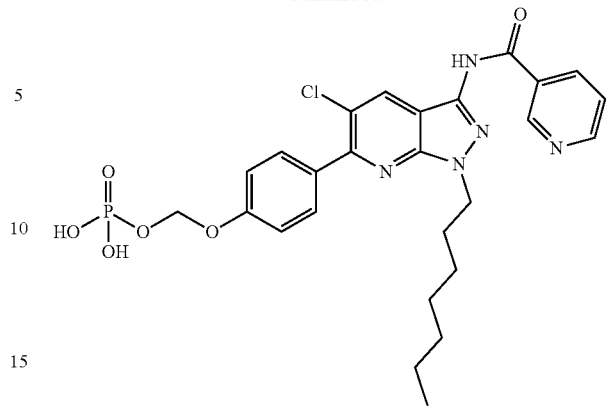

(4-5-chloro-1-heptyl-3-(nicotinamido)-1H-pyrazolo[3,4-b]pyridin-
6-yl)phenoxy)methyl dihydrogen phosphate

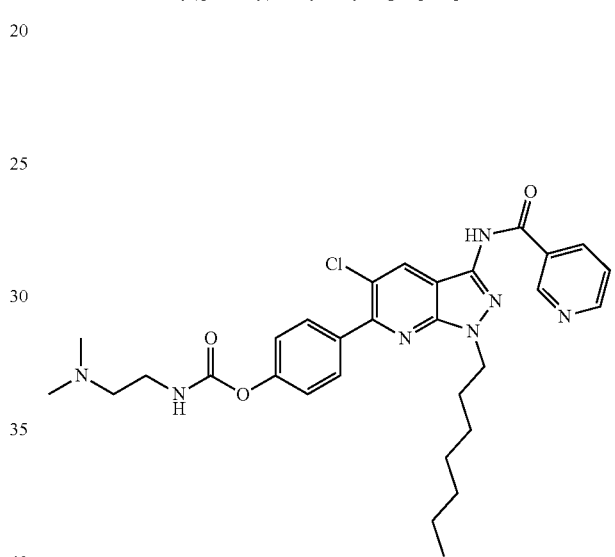

4-(5-chloro-1-heptyl-3-(nicotinamido)-1H-pyrazolo[3,4-b]pyridin-
6-yl)phenyl (2-(dimethylamino)ethyl)carbamate

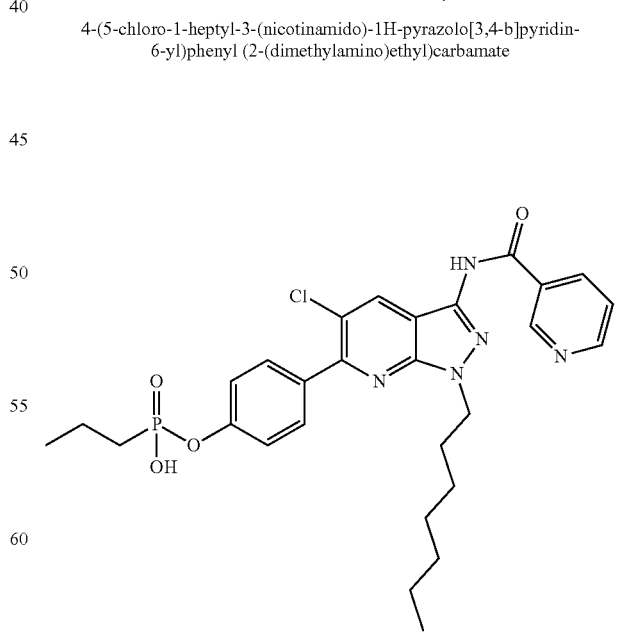

4-(5-chloro-1-heptyl-3-(nicotinamido)-1H-pyrazolo[3,4-b]pyridin-
6-yl)phenyl hydrogen propylphosphonate

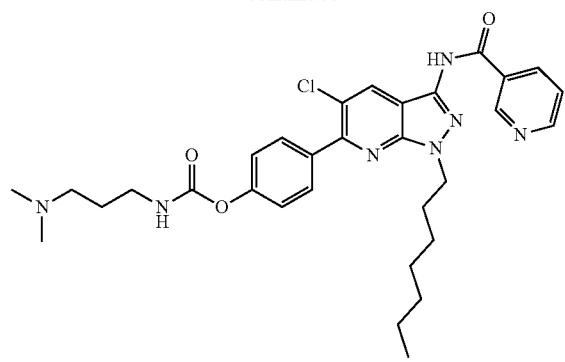

4-(5-chloro-1-heptyl-3-(nicotinamido)-1H-pyrazolo[3,4-b]pyridin-6-yl)phenyl (3-(dimethylamino)propyl)carbamate

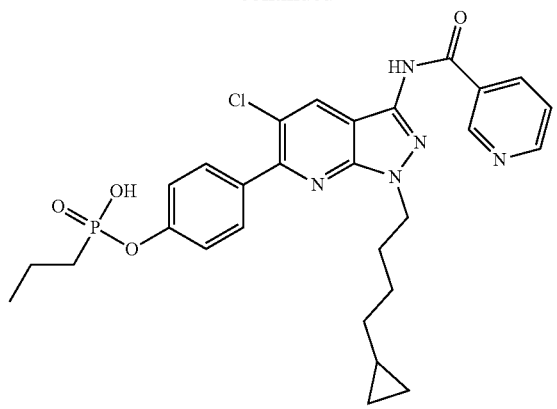

4-(5-chloro-1-(4-cyclopropylbutyl)-3-(nicotinamido)-1H-pyrazolo[3,4-b]pyridin-6-yl)phenyl hydrogen propylphosphonate

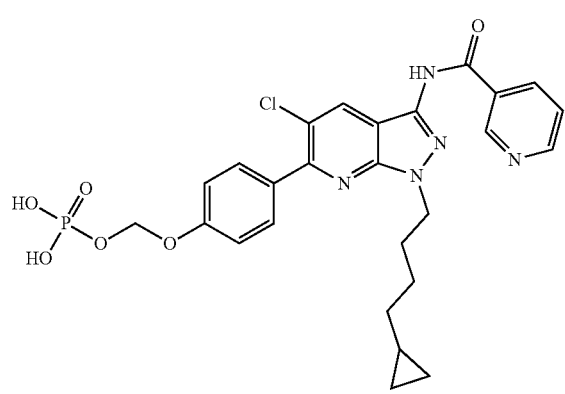

(4-(5-chloro-1-(4-cyclopropylbutyl)-3-(nicotinamido)-1H-pyrazolo[3,4-b]pyridin-6-yl)phenoxy)methyl dihydrogen phosphate

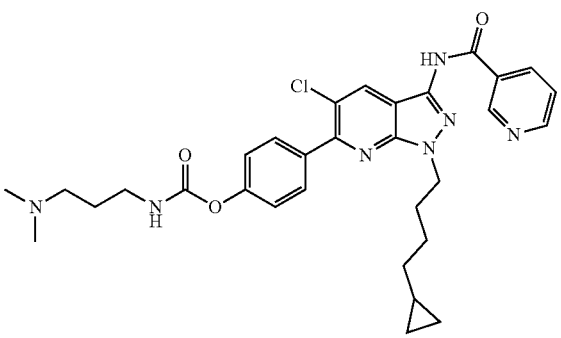

4-(5-chloro-1-(4-cyclopropylbutyl)-3-(nicotinamido)-1H-pyrazolo[3,4-b]pyridin-6-yl)phenyl (3-(dimethylamino)propyl)carbamate

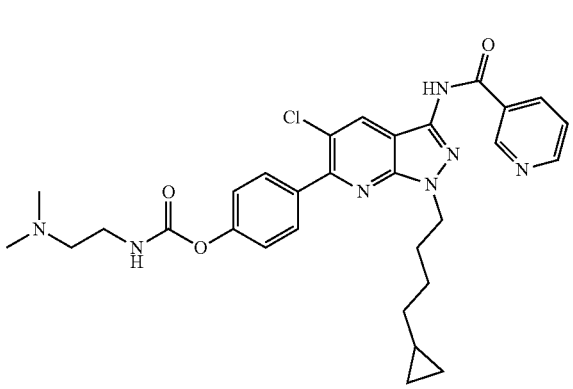

4-(5-chloro-1-(4-cyclopropylbutyl)-3-(nicotinamido)-1H-pyrazolo[3,4-b]pyridin-6-yl)phenyl (2-(dimethylamino)ethyl)carbamate

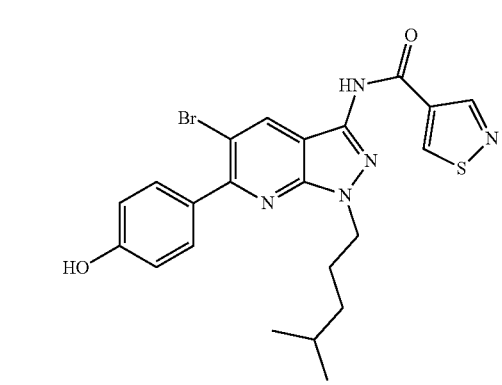

N-(5-bromo-6-(4-hydroxyphenyl)-1-(4-methylpentyl)-1H-pyrazolo[3,4-b]pyridin-3-yl)isothiazole-4-carboxamide

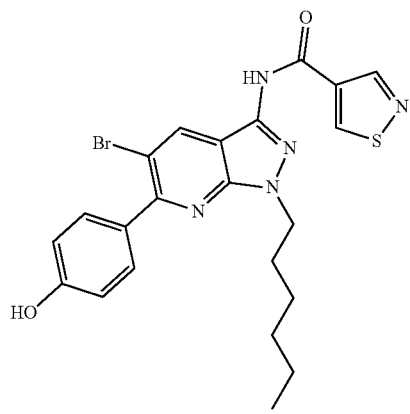

N-(5-bromo-1-hexyl-6-(4-hydroxyphenyl)-1H-pyrazolo[3,4-b]pyridin-3-yl)isothiazole-4-carboxamide

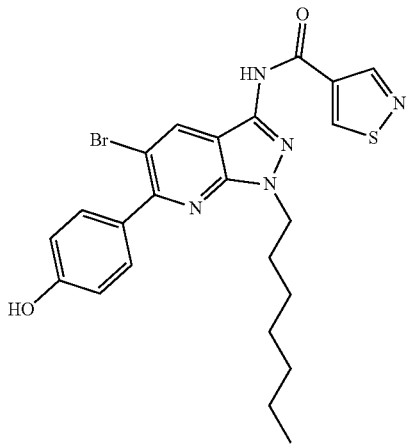

N-(5-bromo-1-heptyl-6-(4-hydroxyphenyl)-1H-parazolo[3,4-b]pyridin-3-yl)isothiazole-4-carboxamide

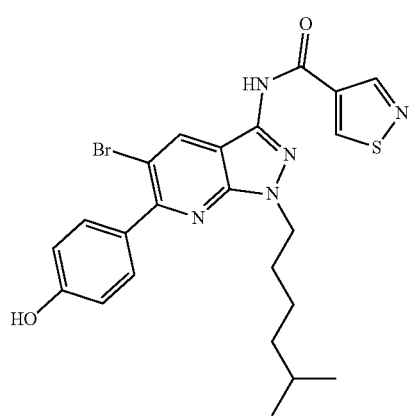

N-(5-bromo-6-(4-hydroxyphenyl)-1-(5-methylhexyl)-1H-pyrazolol[3,4-b]pyridin-3-yl)isothiazole-4-carboxamide

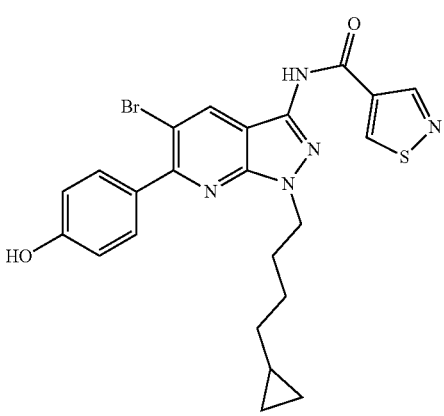

N-(5-bromo-1-(4-cyclopropylbutyl)-6-(4-hydroxyphenyl)-1H-pyrazolo[3,4-b]pyridin-3-yl)isothiazole-4-carboxamide

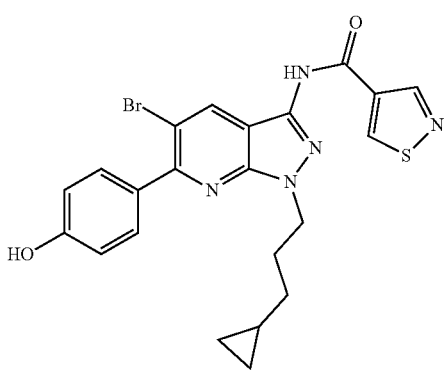

N-(5-bromo-1-(3-cyclopropylpropyl)-6-(4-hydroxyphenyl)-1H-pyrazolo[3,4-b]pyridin-3-yl)isothiazole-4-carboxamide

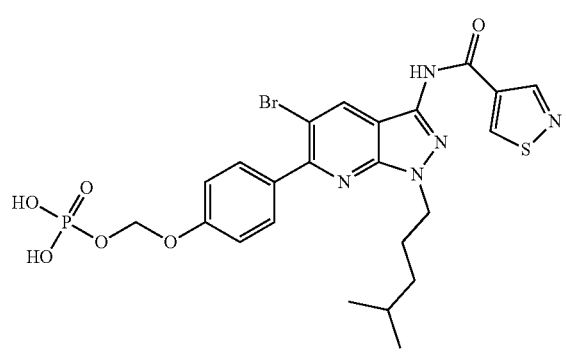

(4-(5-bromo-3-(isothiazole-4-carboxamido)-1-(4-methylpentyl)-1H-pyrazolo[3,4-b]pyridin-6-yl)phenoxy)methyl dihydrogen phosphate 27
-continued

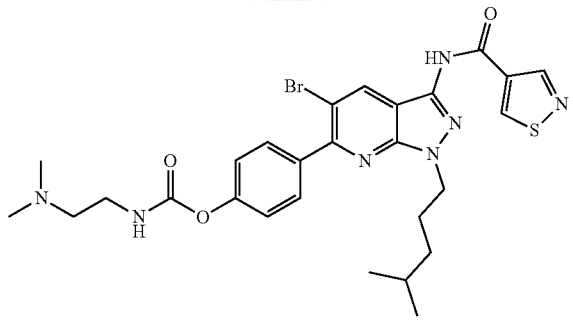

4-(5-bromo-3-(isothiazole-4-carboxamido)-1-(4-methylpentyl)-1H-pyrazolo[3,4-b]pyridin-6-yl)phenyl (2-(dimethylamino)ethyl)carbamate

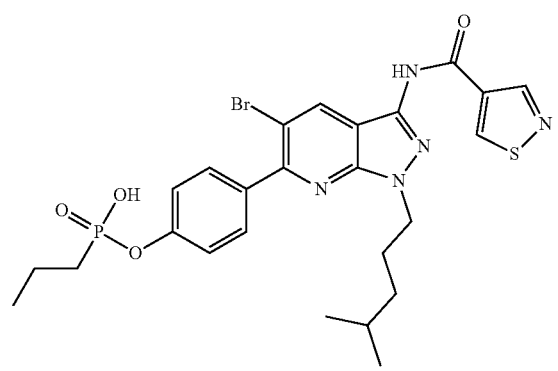

4-(5-bromo-3-(isothiazole-4-carboxamido)-1-(4-methylpentyl)-1H-pyrazolo[3,4-b]pyridin-6-yl)phenyl hydrogen propylphosphonate

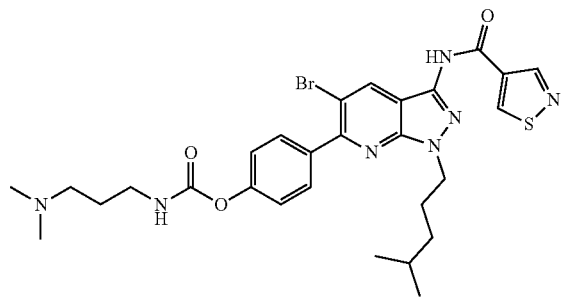

4-(5-bromo-3-(isothiazole-4-carboxamido)-1-(4-methylpentyl)-1H-pyrazolo[3,4-b]pyridin-6-yl)phenyl (3-(dimethylamino)propyl)carbamate

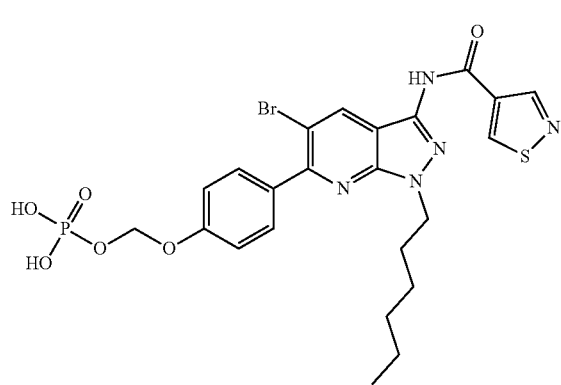

(4-(5-bromo-1-hexyl-3-(isothiazole-4-carboxamido)-1H-pyrazolo[3,4-b]pyridin-6-yl)phenoxy)methyl dihydrogen phosphate 28
-continued

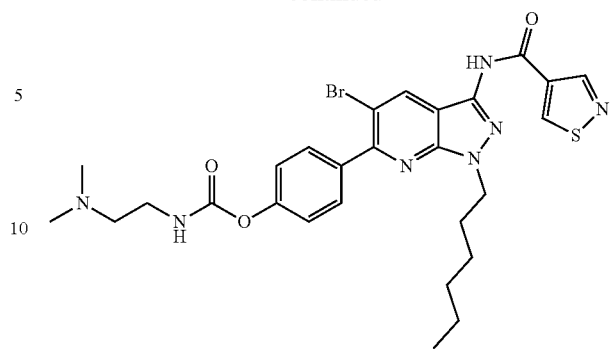

4-(5-bromo-1-hexyl-3-(isothiazole-4-carboxamido)-1H-pyrazolo[3,4-b]pyridin-6-yl)phenyl (2-(dimethylamino)ethyl)carbamate

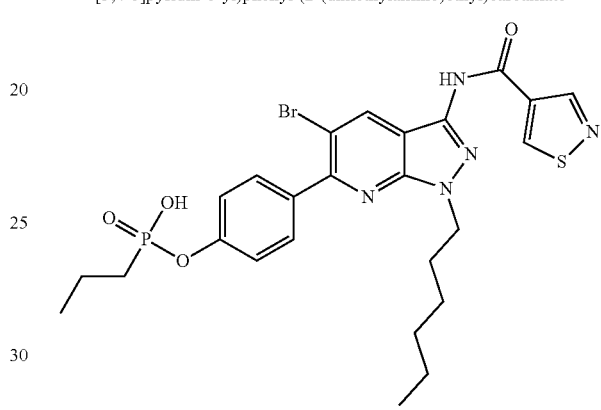

4-(5-bromo-1-hexyl-3-(isothiazole-4-carboxamido)-1H-pyrazolo[3,4-b]pyridin-6-yl)phenyl hydrogen propylphosphonate

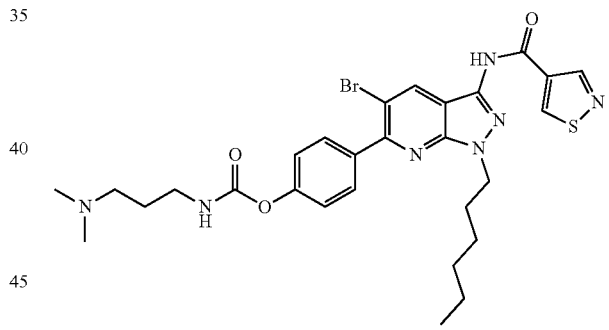

4-(5-bromo-1-hexyl-3-(isothiazole-4-carboxamido)-1H-pyrazolo[3,4-b]pyridin-6-yl)phenyl (3-(dimethylamino)propyl)carbamate

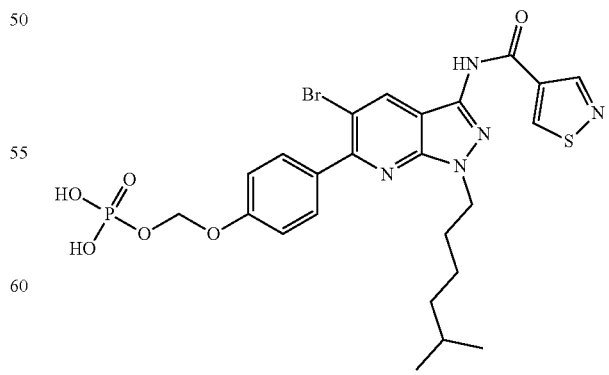

(4-(5-bromo-3-(isothiazole-4-carboxamido)-1-(5-methylhexyl)-1H-pyrazolo[3,4-b]pyridin-6-yl)phenoxy)methyl dihydrogen phosphate

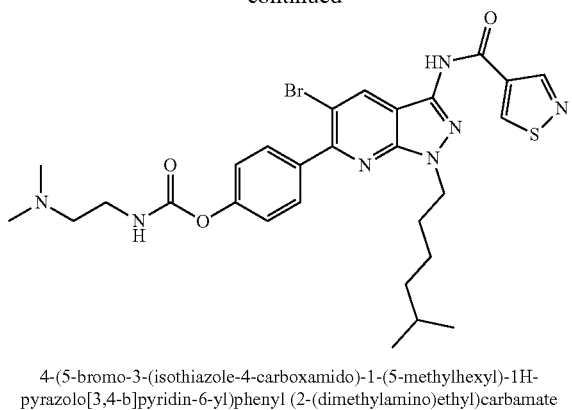

4-(5-bromo-3-(isothiazole-4-carboxamido)-1-(5-methylhexyl)-1H-pyrazolo[3,4-b]pyridin-6-yl)phenyl (2-(dimethylamino)ethyl)carbamate

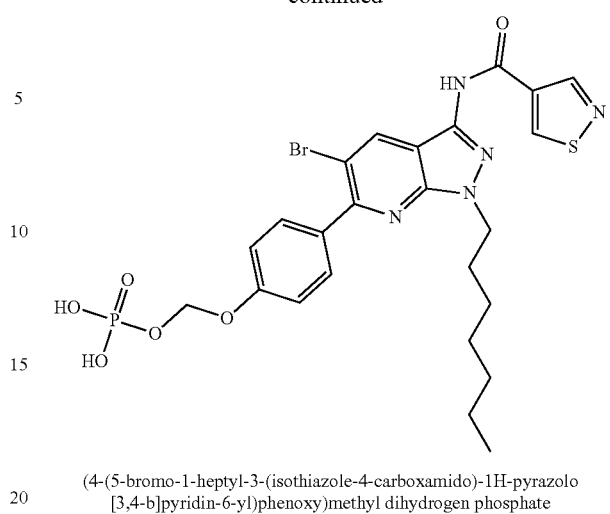

(4-(5-bromo-1-heptyl-3-(isothiazole-4-carboxamido)-1H-pyrazolo[3,4-b]pyridin-6-yl)phenoxy)methyl dihydrogen phosphate

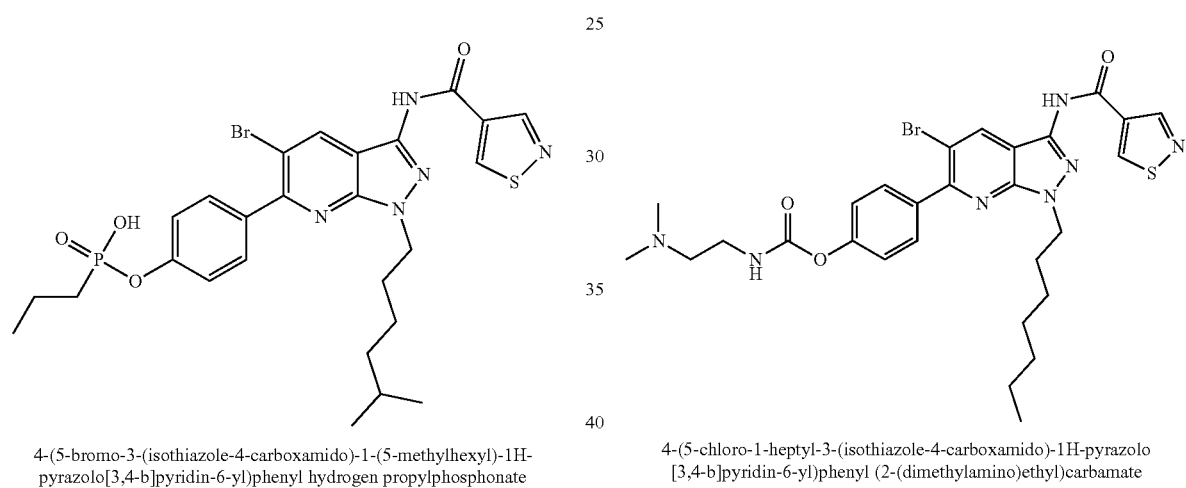

4-(5-bromo-3-(isothiazole-4-carboxamido)-1-(5-methylhexyl)-1H-pyrazolo[3,4-b]pyridin-6-yl)phenyl hydrogen propylphosphonate 4-(5-chloro-1-heptyl-3-(isothiazole-4-carboxamido)-1H-pyrazolo[3,4-b]pyridin-6-yl)phenyl (2-(dimethylamino)ethyl)carbamate

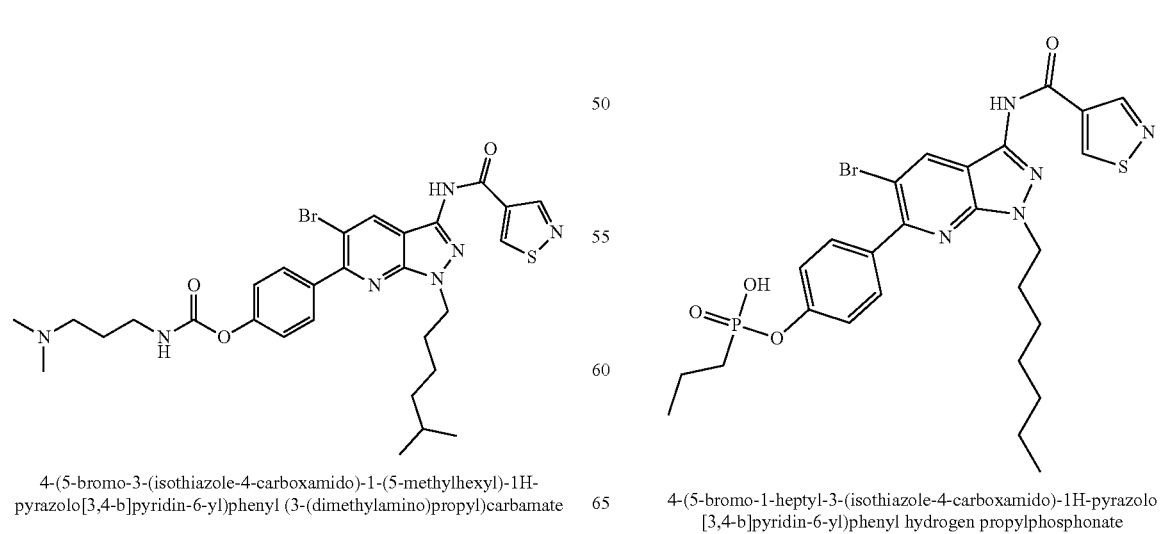

4-(5-bromo-3-(isothiazole-4-carboxamido)-1-(5-methylhexyl)-1H-pyrazolo[3,4-b]pyridin-6-yl)phenyl (3-(dimethylamino)propyl)carbamate 4-(5-bromo-1-heptyl-3-(isothiazole-4-carboxamido)-1H-pyrazolo[3,4-b]pyridin-6-yl)phenyl hydrogen propylphosphonate

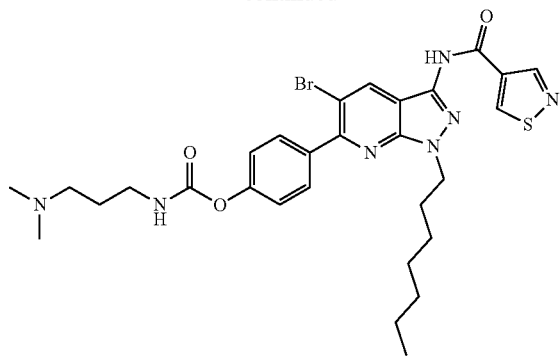

4-(5-bromo-1-heptyl-3-(isothiazole-4-carboxamido)-1H-pyrazolo[3,4-b]pyridin-6-yl)phenyl (3-(dimethylamino)propyl)carbamate

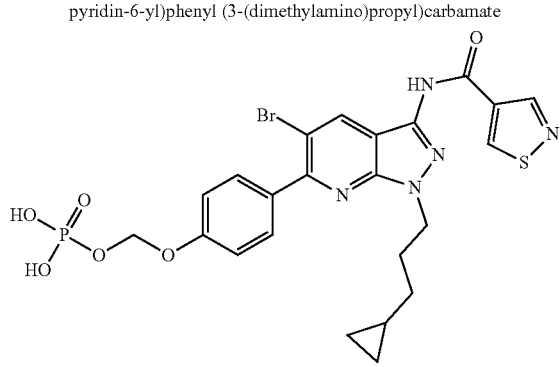

(4-(5-bromo-1-(3-cyclopropylpropyl)-3-(isothiazole-4-carboxamido)-1H-pyrazolo[3,4-b]pyridin-6-yl)phenoxy)methyl dihydrogen phosphate

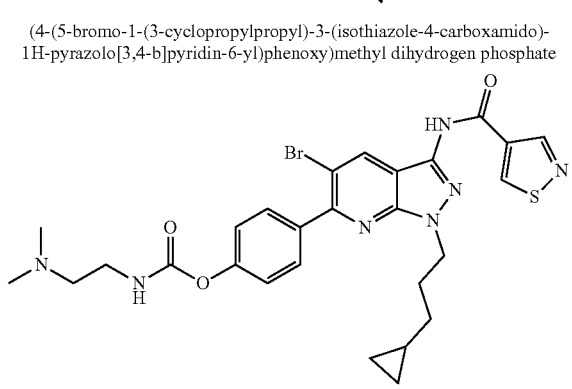

4-(5-bromo-1-(3-cyclopropylpropyl)-3-(isothiazole-4-carboxamido)-1H-pyrazolo[3,4-b]pyridin-6-yl)phenyl (2-(dimethylamino)ethyl)carbamate

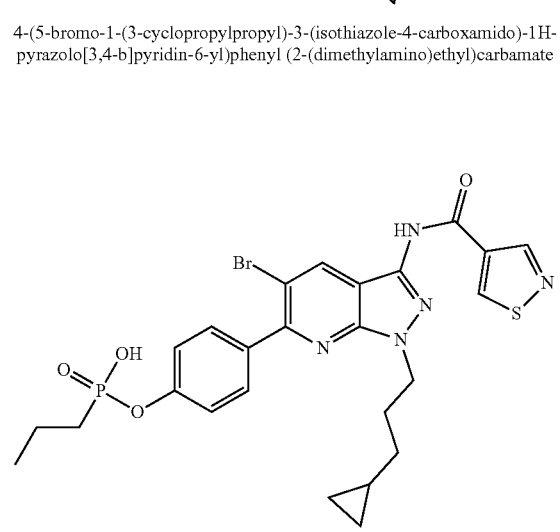

4-(5-bromo-1-(3-cyclopropylpropyl)-3-(isothiazole-4-carboxamido)-1H-pyrazolo[3,4-b]pyridin-6-yl)phenyl hydrogen propylphosphonate

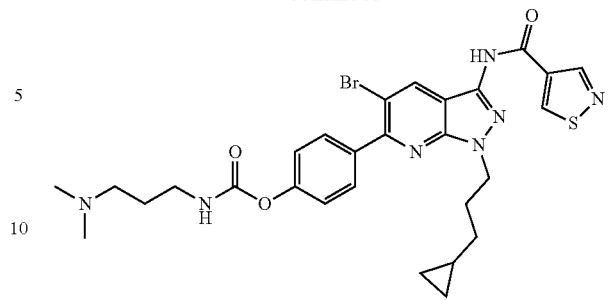

4-(5-bromo-1-(3-cyclopropylpropyl)-3-(isothiazole-4-carboxamido)-1H-pyrazolo[3,4-b]pyridin-6-yl)phenyl (3-(dimethylamino)propyl)carbamate

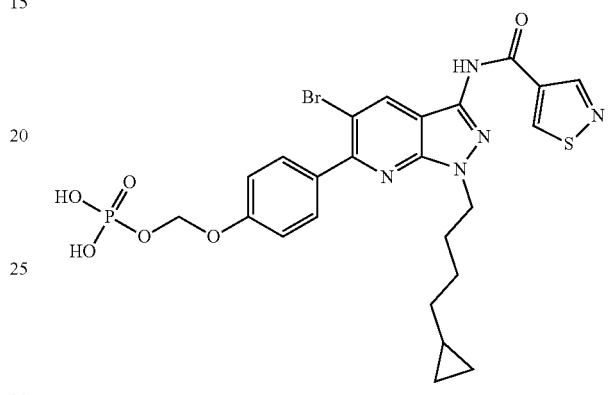

(4-(5-bromo-1-(4-cyclopropylbutyl)-3-(isothiazole-4-carboxamido)-1H-pyrazolo[3,4-b]pyridin-6-yl)phenoxy)methyl dihydrogen phosphate

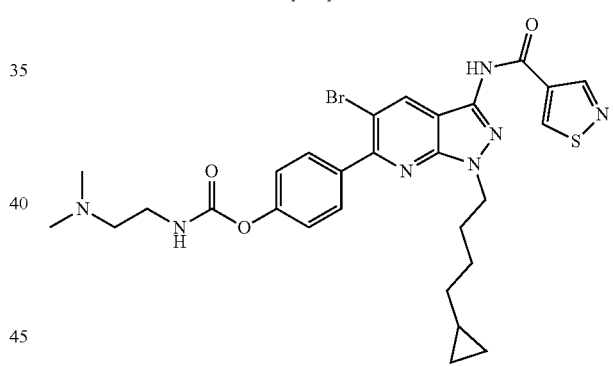

4-(5-bromo-1-(4-cyclopropylbutyl)-3-(isothiazole-4-carboxamido)-1H-pyrazolo[3,4-b]pyridin-6-yl)phenyl (2-(dimethylamino)ethyl)carbamate

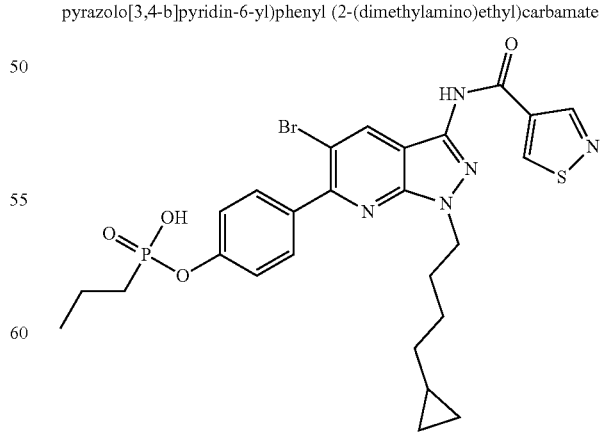

4-(5-bromo-1-(4-cyclopropylbutyl)-3-(isothiazole-4-carboxamido)-1H-pyrazolo[3,4-b]pyridin-6-yl)phenyl hydrogen propylphosphonate

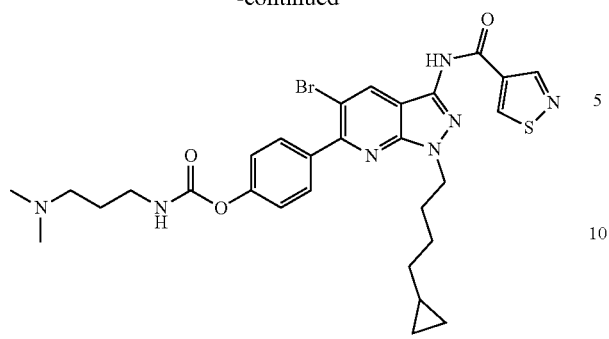

4-(5-bromo-1-(4-cyclopropylbutyl)-3-(isothiazole-4-carboxamido)-1H-pyrazolo[3,4-b]pyridin-6-yl)phenyl (3-(dimethylamino)propyl)carbamate

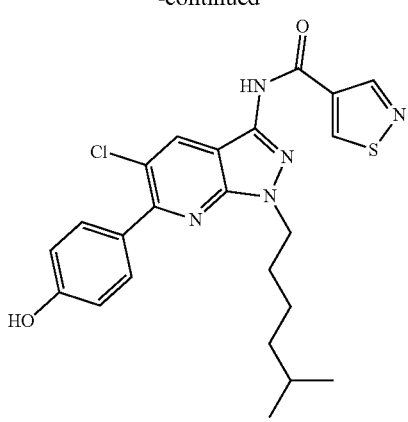

N-(5-chloro-6-(4-hydroxyphenyl)-1-(5-methylhexyl)-1H-pyrazolol[3,4-b]pyridin-3-yl)isothiazole-4-carboxamide

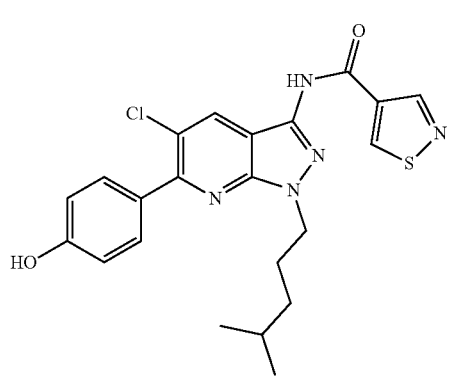

N-(5-chloro-6-(4-hydroxyphenyl)-1-(4-methylpentyl)-1H-pyrazolo[3,4-b]pyridin-3-yl)isothiazole-4-carboxamide

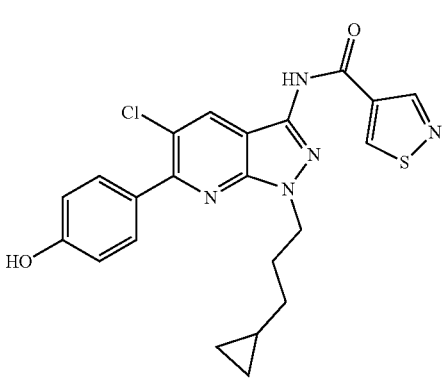

N-(5-chloro-1-(3-cyclopropylpropyl)-6-(4-hydroxyphenyl)-1H-pyrazolo[3,4-b]pyridin-3-yl)isothiazole-4-carboxamide

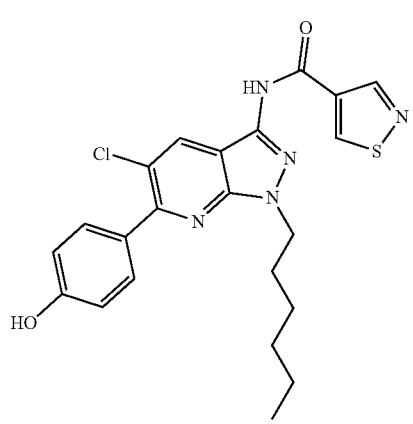

N-(5-chloro-1-hexyl-6-(4-hydroxyphenyl)-1H-pyrazolo[3,4-b]pyridin-3-yl)isothiazole-4-carboxamide

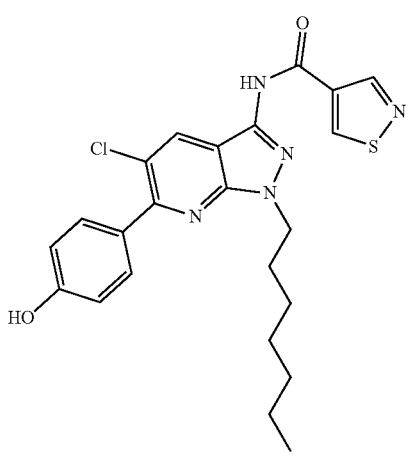

N-(5-chloro-1-heptyl-6-(4-hydroxphenyl)-1H-parazolo[3,4-b]pyridin-3-yl)isothiazole-4-carboxamide

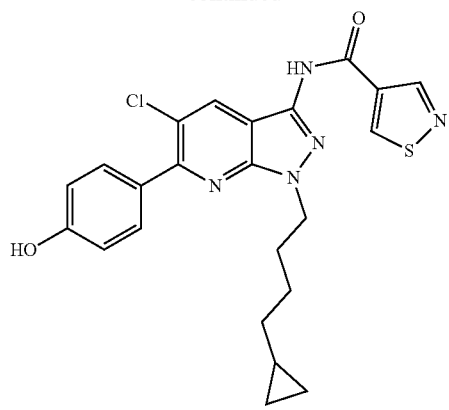

N-(5-chloro-1-(4-cyclopropylbutyl)-6-(4-hydroxyphenyl)-1H-pyrazolo[3,4-b]pyridin-3-yl)isothiazole-4-carboxamide

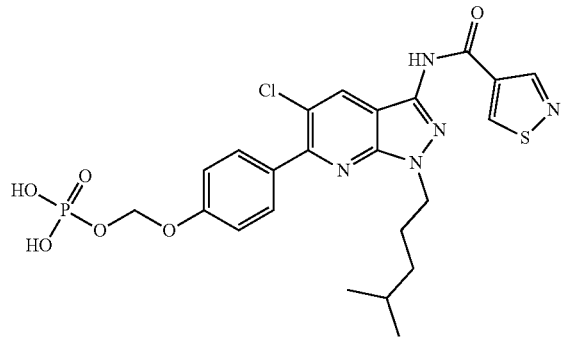

(4-(5-chloro-3-(isothiazole-4-carboxamido)-1-(4-methylpentyl)-1H-pyrazolo[3,4-b]pyridin-6-yl)phenoxy)methyl dihydrogen phosphate

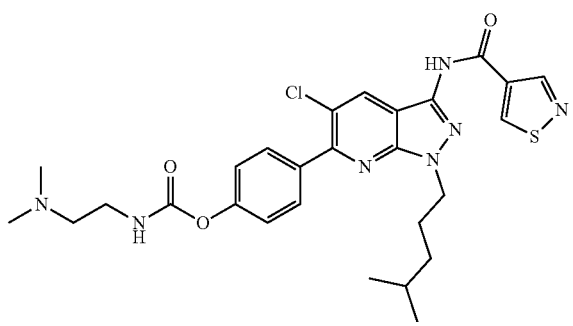

4-(5-chloro-3-(isothiazole-4-carboxamido)-1-(4-methylpentyl)-1H-pyrazolo[3,4-b]pyridin-6-yl)phenyl (2-(dimethylamino)ethyl)carbamate

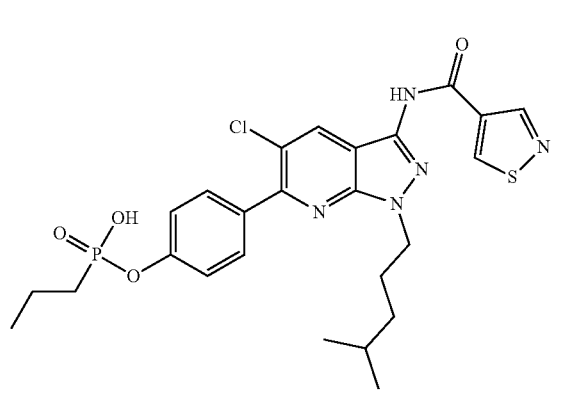

4-(5-chloro-3-(isothiazole-4-carboxamido)-1-(4-methylpentyl)-1H-pyrazolo[3,4-b]pyridin-6-yl)phenyl hydrogen propylphosphonate

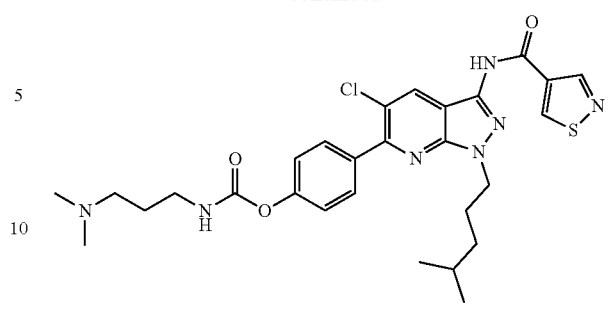

4-(5-chloro-3-(isothiazole-4-carboxamido)-1-(4-methylpentyl)-1H-pyrazolo[3,4-b]pyridin-6-yl)phenyl (3-(dimethylamino)propyl)carbamate

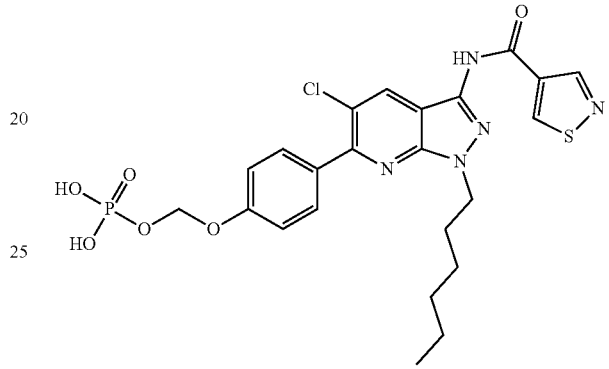

(4-(5-chloro-1-hexyl-3-(isothiazole-4-carboxamido)-1H-pyrazolo[3,4-b]pyridin-6-yl)phenoxy)methyl dihydrogen phosphate

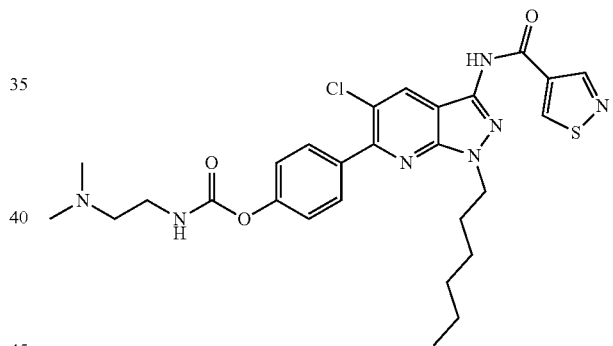

4-(5-chloro-1-hexyl-3-(isothiazole-4-carboxamido)-1H-pyrazolo[3,4-b]pyridin-6-yl)phenyl (2-(dimethylamino)ethyl)carbamate

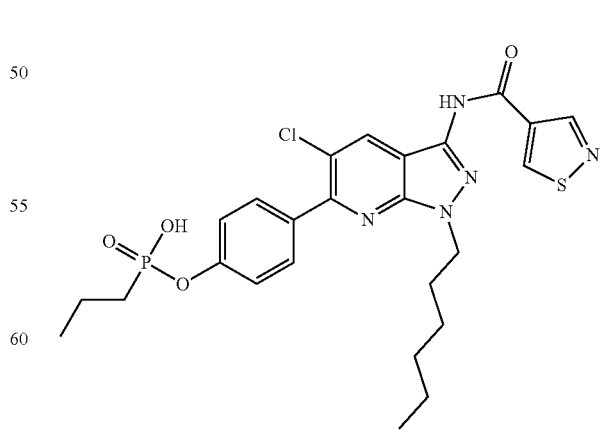

4-(5-chloro-1-hexyl-3-(isothiazole-4-carboxamido)-1H-pyrazolo[3,4-b]pyridin-6-yl)phenyl hydrogen propylphosphonate

37
-continued

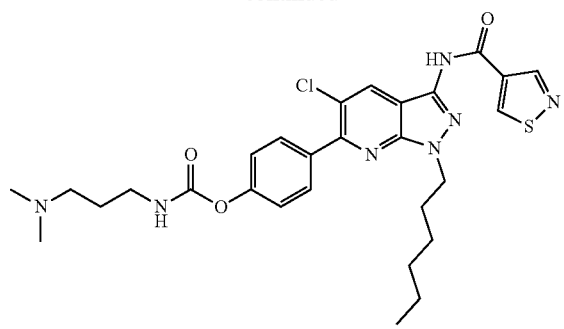

4-(5-chloro-1-hexyl-3-(isothiazole-4-carboxamido)-1H-pyrazolo[3,4-b]pyridin-6-yl)phenyl (3-(dimethylamino)propyl)carbamate

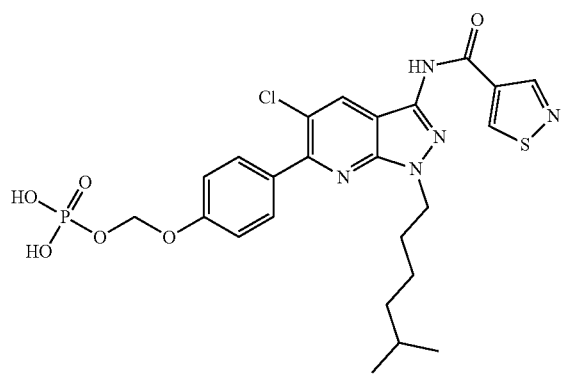

(4-(5-chloro-3-(isothiazole-4-carboxamido)-1-(5-methylhexyl)-1H-pyrazolo[3,4-b]pyridin-6-yl)phenoxy)methyl dihydrogen phosphate

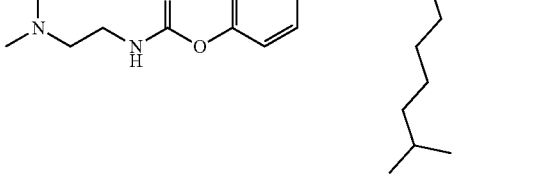

4-(5-chloro-3-(isothiazole-4-carboxamido)-1-(5-methylhexyl)-1H-pyrazolo[3,4-b]pyridin-6-yl)phenyl (2-(dimethylamino)ethyl)carbamate

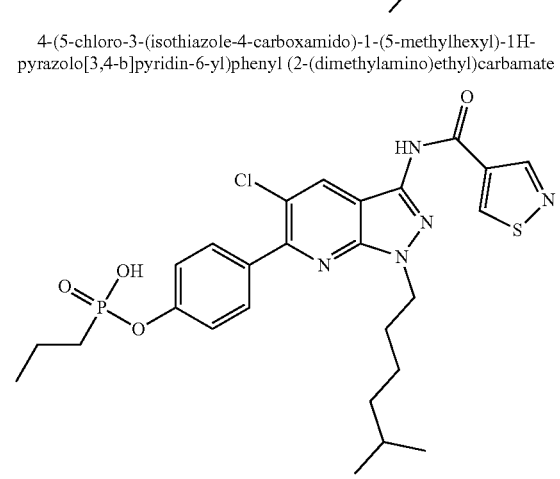

4-(5-chloro-3-(isothiazole-4-carboxamido)-1-(5-methylhexyl)-1H-pyrazolo[3,4-b]pyridin-6-yl)phenyl hydrogen propylphosphonate

38
-continued

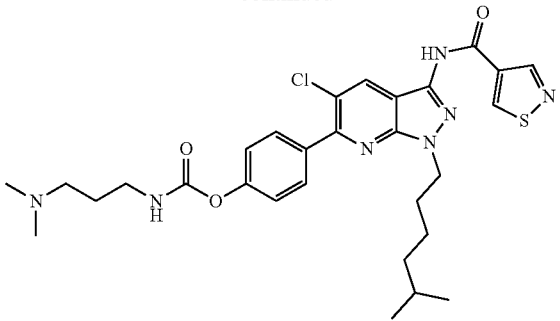

4-(5-chloro-3-(isothiazole-4-carboxamido)-1-(5-methylhexyl)-1H-pyrazolo[3,4-b]pyridin-6-yl)phenyl (3-(dimethylamino)propyl)carbamate

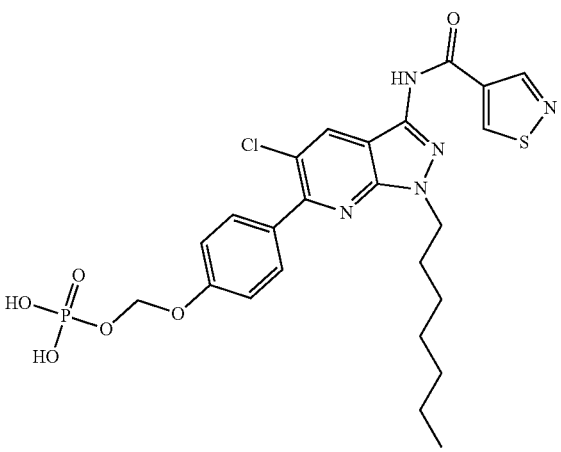

(4-(5-chloro-1-heptyl-3-(isothiazole-4-carboxamido)-1H-pyrazolo[3,4-b]pyridin-6-yl)phenoxy)methyl dihydrogen phosphate

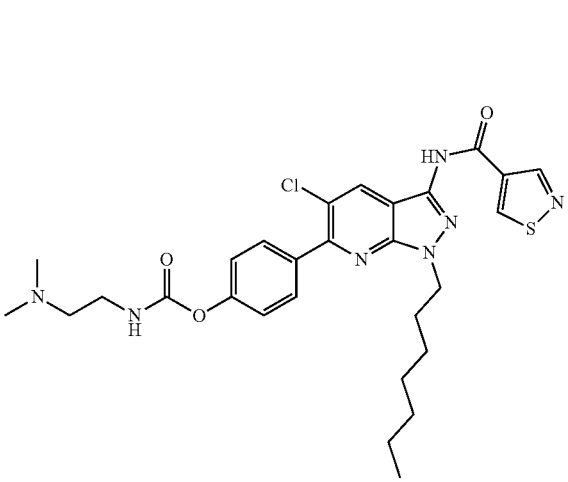

4-(5-chloro-1-heptyl-3-(isothiazole-4-carboxamido)-1H-pyrazolo[3,4-b]pyridin-6-yl)phenyl (2-(dimethylamino)ethyl)carbamate

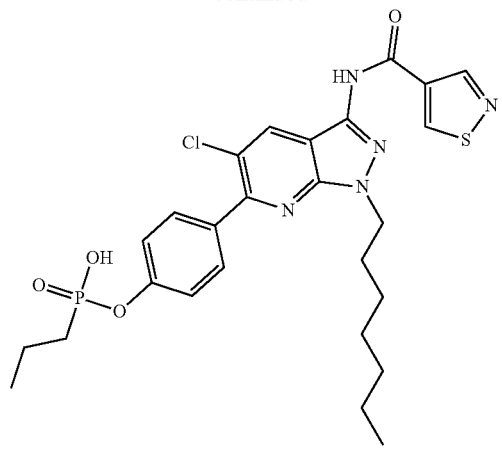

4-(5-chloro-1-heptyl-3-(isothiazole-4-carboxamido)-1H-pyrazolo[3,4-b]pyridin-6-yl)phenyl hydrogen propylphosphonate

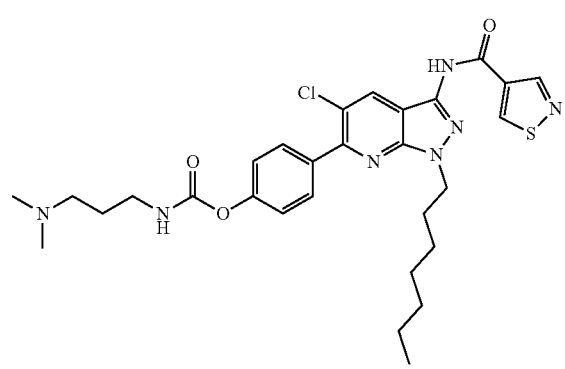

4-(5-chloro-1-heptyl-3-(isothiazole-4-carboxamido)-1H-pyrazolo[3,4-b]pyridin-6-yl)phenyl (3-(dimethylamino)propyl)carbamate

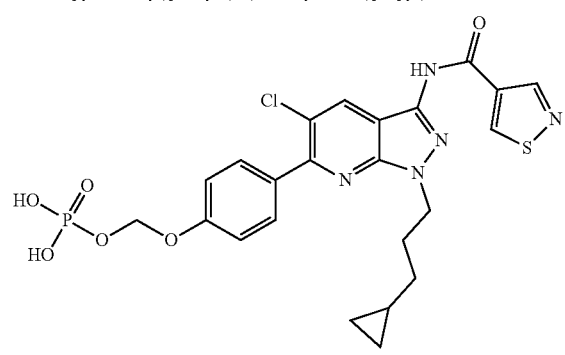

(4-(5-chloro-1-(3-cyclopropylpropyl)-3-(isothiazole-4-carboxamido)-1H-pyrazolo[3,4-b]pyridin-6-yl)phenoxy)methyl dihydrogen phosphate

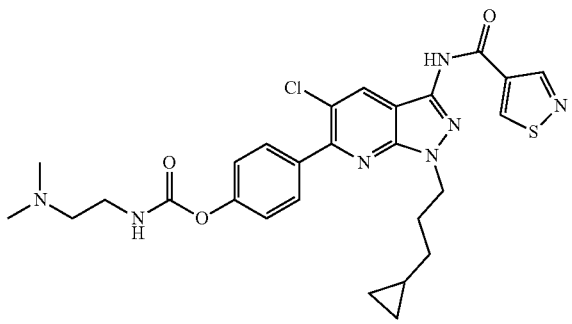

4-(5-chloro-1-(3-cyclopropylpropyl)-3-(isothiazole-4-carboxamido)-1H-pyrazolo[3,4-b]pyridin-6-yl)phenyl (2-(dimethylamino)ethyl)carbamate

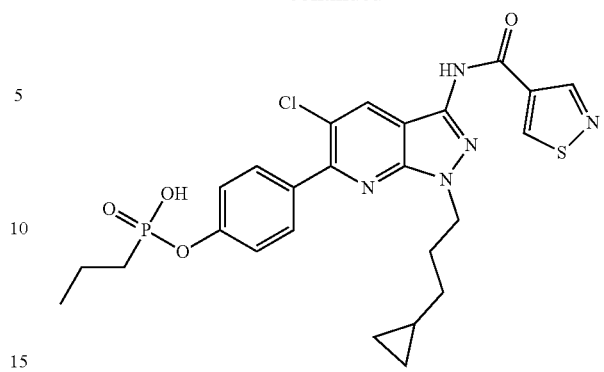

4-(5-chloro-1-(3-cyclopropylpropyl)-3-(isothiazole-4-carboxamido)-1H-pyrazolo[3,4-b]pyridin-6-yl)phenyl hydrogen propylphosphonate

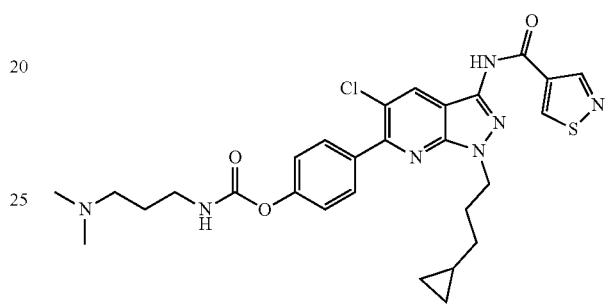

4-(5-chloro-1-(3-cyclopropylpropyl)-3-(isothiazole-4-carboxamido)-1H-pyrazolo[3,4-b]pyridin-6-yl)phenyl (3-(dimethylamino)propyl)carbamate

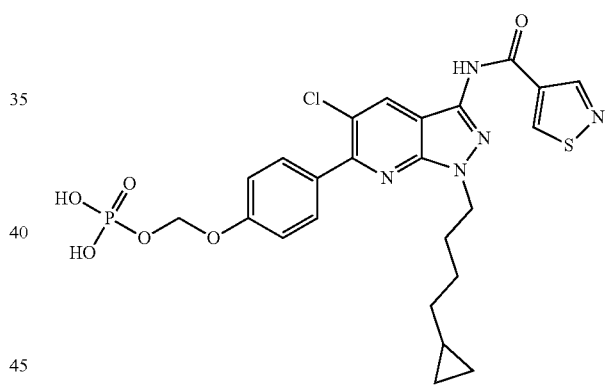

(4-(5-chloro-1-(4-cyclopropylbutyl)-3-(isothiazole-4-carboxamido)-1H-pyrazolo[3,4-b]pyridin-6-yl)phenoxy)methyl dihydrogen phosphate

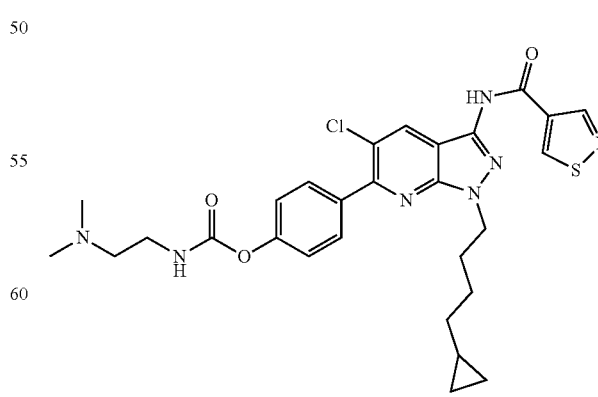

4-(5-chloro-1-(4-cyclopropylbutyl)-3-(isothiazole-4-carboxamido)-1H-pyrazolo[3,4-b]pyridin-6-yl)phenyl (2-(dimethylamino)ethyl)carbamate -continued

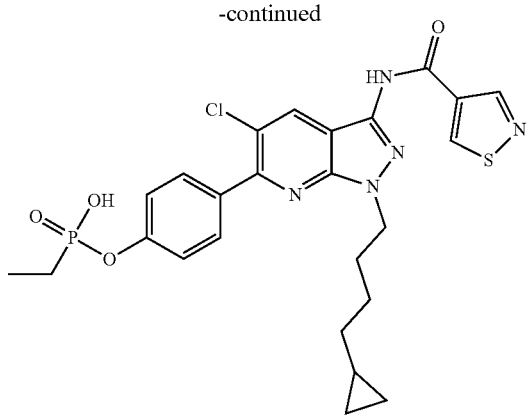

4-(5-chloro-1-(4-cyclopropylbutyl)-3-(isothiazole-4-carboxamido)-1H-pyrazolo[3,4-b]pyridin-6-yl)phenyl hydrogen propylphosphonate

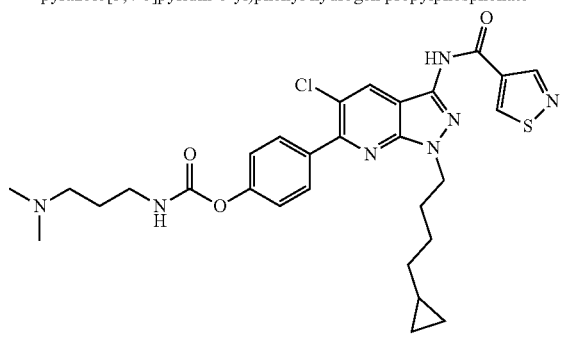

4-(5-chloro-1-(4-cyclopropylbutyl)-3-(isothiazole-4-carboxamido)-1H-pyrazolo[3,4-b]pyridin-6-yl)phenyl (3-(dimethylamino)propyl)carbamate In some embodiments, a method of synthesizing an antiviral compound in according with the structures provided herein can be performed. The method can include: obtaining 6-(4-methoxyphenyl)-2-oxo-1,2-dihydropyridine-3-carbonitrile; reacting the 6-(4-methoxyphenyl)-2-oxo-1,2-dihydropyridine-3-carbonitrile with a halogenated succinimide to form the structure of Formula 2:

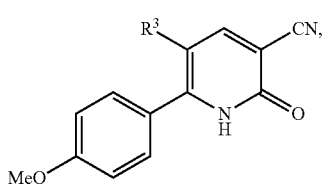

Formula 2 wherein $R^3$ is the halogen; reacting the compound of Formula 2 to form the compound of Formula 3:

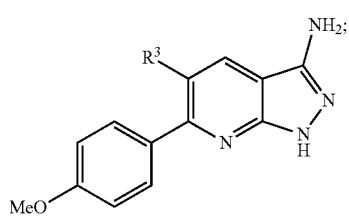

Formula 3 reacting the compound of Formula 3 to form the compound of Formula 4:

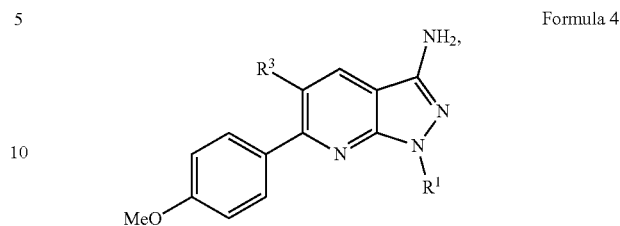

Formula 4 wherein $R^1$ is hydrogen or a substituent; reacting the compound of Formula 4 to form the compound of Formula 5:

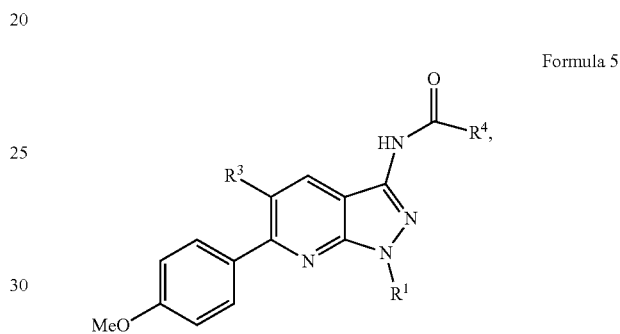

Formula 5 wherein $R^4$ includes a heterocycle; and reacting the compound of Formula 5 to form the compound of Formula 6:

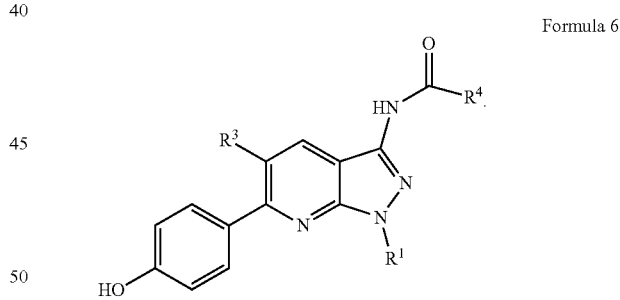

Formula 6

In some embodiments, the synthetic method can include: reacting the compound of Formula 2 with POCl$_3$ in DMF and with N$_2$H$_2$·H$_2$O in EtOH form the compound of Formula 3; reacting the compound of Formula 3 with an alkyl halide to form the compound of Formula 4; reacting the compound of Formula 4 with a nicotinoyl chloride hydrochloride or isothiazole-4-carboxylic acid to form the compound of Formula 5; and reacting the compound of Formula 5 with boron tribromide to form the compound of Formula 6.

In some embodiments, a method of synthesizing a prodrug compound can include: obtaining the compound of Formula 6; and performing one of: reacting the compound of Formula 6 to form a carbamate prodrug of Formula 7:

Formula 7

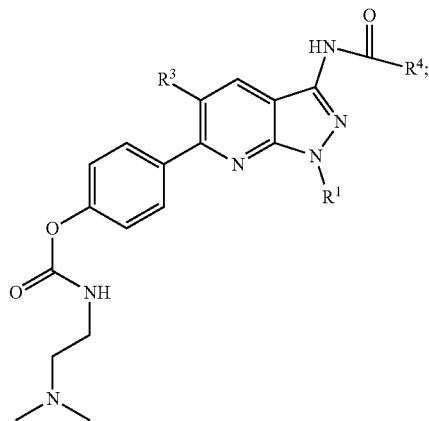

reacting the compound of Formula 6 to form an alkyl phosphonate prodrug of Formula 8:

Formula 8

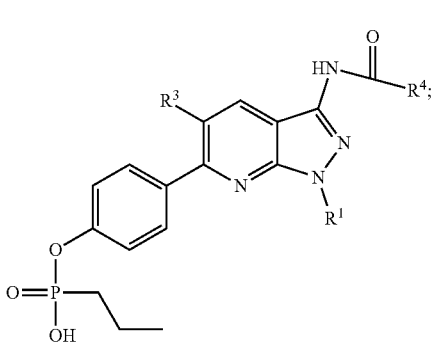

or reacting the compound of Formula 6 to form an methylene phosphate prodrug of Formula 9:

Formula 9

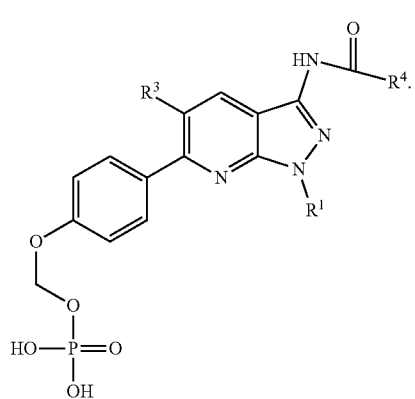

In some embodiments, the method of forming the prodrug can include one of: reacting the compound of Formula 6 with Carbonyldiimidazole, pyridine and N1,N1-dimethylethane-1,2-diamine to form a carbamate prodrug of Formula 7; reacting the compound of Formula 6 with 2,4,6-tripropyl-1,3,5,2,4,6-trioxatriphosphinane 2,4,6-trioxide to form an alkyl phosphonate prodrug of Formula 8; or reacting the compound of Formula 6 with di-tert-butyl chloromethyl phosphate to form an methylene phosphate prodrug of Formula 9.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g. alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g. $Na^+$, $Li^+$, $K^+$, $Ca^{2+}$, $Mg^{2+}$, $Zn^{2+}$), ammonia or organic amines (e.g. dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

In a related aspect, a pharmaceutical composition is provided, the pharmaceutical composition including an effective amount of the compound of any embodiments of compounds of the formulae (or pharmaceutically acceptable salt thereof) for treating a condition; and where the condition is infection with a virus. The virus can be any one or more of those listed herein.

The instant present technology provides pharmaceutical compositions and medicaments comprising any of the compounds of the formulae disclosed herein and optionally a pharmaceutically acceptable carrier or one or more excipients or fillers. The compositions may be used in the methods and treatments described herein. Such compositions and medicaments include a therapeutically effective amount of any compound as described herein. The pharmaceutical composition may be packaged in unit dosage form.

The pharmaceutical compositions and medicaments may be prepared by mixing one or more compounds of the present technology, pharmaceutically acceptable salts thereof, stereoisomers thereof, tautomers thereof, or solvates thereof, with pharmaceutically acceptable carriers, excipients, binders, diluents or the like.

The pharmaceutical compositions can be in the form of, for example, granules, powders, tablets, capsules, syrup, suppositories, injections, emulsions, elixirs, suspensions or solutions. The instant compositions can be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections. The following dosage forms are given by way of example and should not be construed as limiting the instant present technology.

Besides those representative dosage forms described above, pharmaceutically acceptable excipients and carriers are generally known to those skilled in the art and are thus included in the instant present technology. Such excipients and carriers are described, for example, in "Remington's Pharmaceutical Sciences" Mack Pub. Co., New Jersey (1991), which is incorporated herein by reference.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Those skilled in the art are readily able to determine an effective amount, such as by simply administering a compound of the present technology to a patient in increasing amounts until the progression of the condition/disease state is decreased or stopped. The compounds of the present technology can be administered to a patient at dosage levels in the range of about 0.1 to about 1,000 mg per day. For a normal human adult having a body weight of about 70 kg, a dosage in the range of about 0.01 to about 100 mg per kg of body weight per day is sufficient. The specific dosage used, however, can vary or may be adjusted as considered appropriate by those of ordinary skill in the art. For example, the dosage can depend on a number of factors including the requirements of the patient, the severity of the condition being treated and the pharmacological activity of the compound being used. The determination of optimum dosages for a particular patient is well known to those skilled in the art.

Various assays and model systems can be readily employed to determine the therapeutic effectiveness of the treatment according to the present technology.

The administration may include oral administration, parenteral administration, or nasal administration. In any of these embodiments, the administration may include subcutaneous injections, intravenous injections, intraperitoneal injections, or intramuscular injections. In any of these embodiments, the administration may include oral administration. The methods of the present technology can also comprise administering, either sequentially or in combination with one or more compounds of the present technology, a conventional therapeutic agent in an amount that can potentially or synergistically be effective for the treatment of the viral infection.

In one aspect, a compound of the present technology is administered to a patient in an amount or dosage suitable for therapeutic use. Generally, a unit dosage comprising a compound of the present technology will vary depending on patient considerations. Such considerations include, for example, age, protocol, condition, sex, extent of disease, contraindications, concomitant therapies and the like. An exemplary unit dosage based on these considerations can also be adjusted or modified by a physician skilled in the art.

For example, a unit dosage for a patient comprising a compound of the present technology can vary from $1\times10^{-4}$ g/kg to 1 g/kg, preferably, $1\times10^{-3}$ g/kg to 1.0 g/kg. Dosage of a compound of the present technology can also vary from 0.01 mg/kg to 100 mg/kg or, preferably, from 0.1 mg/kg to 10 mg/kg.

The antiviral compounds can be used to treat a viral infection, wherein the virus is selected from: Semliki Forest virus complex (e.g., Chikungunya virus), Venezuelan equine encephalitis complex (e.g., Venezuelan equine encephalitis virus), Eastern equine encephalitis complex, Western equine encephalitis complex (Eastern equine encephalitis virus [seven antigenic types]), and flaviviruses (e.g., Dengue virus, Zika virus, Yellow Fever Virus, West Nile Virus, Corona Virus, Flu Virus, Japanese B encephalitis virus), or combinations thereof.

EXAMPLES

Representative compounds according to the formulae and structures provided herein were tested for viral inhibitory activity.

CHIKV 181/25 Virus (Vero Cells)

The compounds defined below were compared with and without a halogen at the $R^3$ substituent position, as shown in FIG. 1. The following control compounds with $R^3$ being hydrogen were tested for activity to the Chikungunya virus (CHIKV 181/25) in Vero cells: $R^1$ is isohexyl, $R^2$ is OH, $R^3$ is H, and $R^4$ is pyridinyl (nicotinyl)—open square data in FIG. 1; $R^1$ is heptyl, $R^2$ is OH, $R^3$ is H, and $R^4$ is isothiazolyl—open circle data in FIG. 1; $R^1$ is hexyl, $R^2$ is OH, $R^3$ is H, and $R^4$ is pyridinyl—open triangle data in FIG. 1. The following antiviral compounds with $R^3$ being a halogen were tested: $R^1$ is isohexyl, $R^2$ is OH, $R^3$ is Cl, and $R^4$ is pyridinyl—closed circle data in FIG. 1 (dark circle with white spot at top left); $R^1$ is heptyl, $R^2$ is OH, $R^3$ is Br, and $R^4$ is 4-carboxyisothiazolyl—filled square data in FIG. 1; $R^1$ is hexyl, $R^2$ is OH, $R^3$ is Br, and $R^4$ is pyridinyl—filled circle data in FIG. 1.

The data in FIG. 1 shows a significant improvement in antiviral inhibitory activity against Chikungunya virus (CHIKV 181/25) in Vero cells when replacing the $R^3$ hydrogen with a halogen. Thus, the compounds provided herein can be used as antiviral compounds against at least Chikungunya virus in view of the inhibitory activity.

DENV-2/S16803 Virus (Vero Cells)

Figure 2:
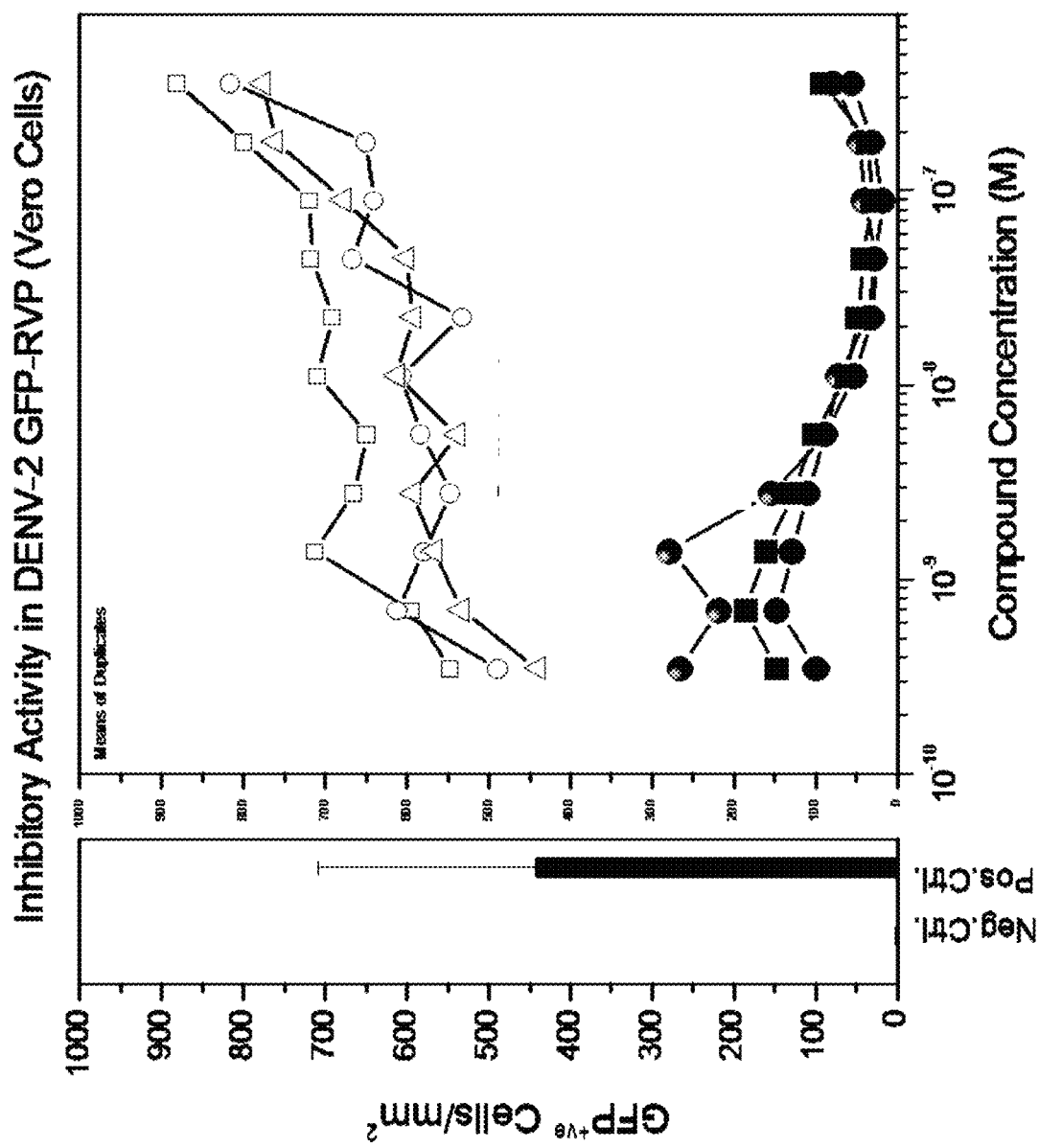
FIG. 2 includes a graph that shows the antiviral inhibitory activity of the compounds described herein for the Yellow Fever Virus.

The compounds defined below were compared with and without a halogen at the $R^3$ substituent position, as shown in FIG. 2. The following control compounds with $R^3$ being hydrogen were tested for activity to the Dengue Serotype 2 virus (DENV-2/S16803) in Vero cells: $R^1$ is isohexyl, $R^2$ is OH, $R^3$ is H, and $R^4$ is pyridinyl—open square data in FIG. 1; $R^1$ is heptyl, $R^2$ is OH, $R^3$ is H, and $R^4$ is 4-carboxyisothiazolyl—open circle data in FIG. 1; $R^1$ is hexyl, $R^2$ is OH, $R^3$ is H, and $R^4$ is pyridinyl—open triangle data in FIG. 1. The following antiviral compounds with $R^3$ being a halogen were tested: $R^1$ is isohexyl, $R^2$ is OH, $R^3$ is Cl, and $R^4$ is pyridinyl—closed circle data in FIG. 1; $R^1$ is heptyl, $R^2$ is OH, $R^3$ is Br, and $R^4$ is 4-carboxyisothiazolyl—filled square data in FIG. 1; $R^1$ is hexyl, $R^2$ is OH, $R^3$ is Br, and $R^4$ is pyridinyl—filled circle data in FIG. 1.

The data in FIG. 2 shows a significant improvement in antiviral inhibitory activity against Dengue Serotype 2 virus (DENV-2/S16803) in Vero cells when replacing the $R^3$ hydrogen with a halogen. Thus, the compounds provided herein can be used as antiviral compounds against at least Dengue virus in view of the inhibitory activity.

SYNTHESIS

Antiviral Compounds

Chemistry. All of the solvents and reagents used were obtained commercially and used as such unless otherwise mentioned. Solvents were removed under reduced pressure using standard rotary evaporators. Flash column chromatography was carried out using RediSep Rf "Gold" high performance silica columns or RediSep Rf $C_{18}$ reverse phase columns on Combiflash Rf instruments unless noted otherwise; thin-layer chromatography was carried out on silica gel CCM precoated aluminum sheets. Purity for all final compounds was confirmed to be greater than 98% by LC-MS using a Zorbax Eclipse Plus 4.6 mm×150 mm, 5 µm analytical reverse phase C column with $H_2O$—$CH_3CN$ and $H_2O$-MeOH gradients and an Agilent 6520 ESI-QTOF accurate mass spectrometer (mass accuracy of 5 ppm) operating in the positive ion acquisition mode.

The syntheses of N-(1-alkyl-5-halo-6-(4-hydroxyphenyl)-1H-pyrazolo[3,4-b]pyridin-3-yl)arylamide analogues were undertaken, as described below, utilizing the strategy by J. Witherington, et al. J. Witherington, V. Bordas, A. Gaiba, N. S. Garton, A. Naylor, A. D. Rawlings, B. P. Slingsby, D. G. Smith, A. K. Takle, R. W. Ward. 6-aryl-pyrazolo[3,4-b] pyridines: potent inhibitors of glycogen synthase kinase-3 (GSK-3), Bioorg Med Chem Lett. 2003 Sep. 15; 13(18): 3055-3057. doi: 10.1016/s0960-894x(03)00645-0.

Figure 3:
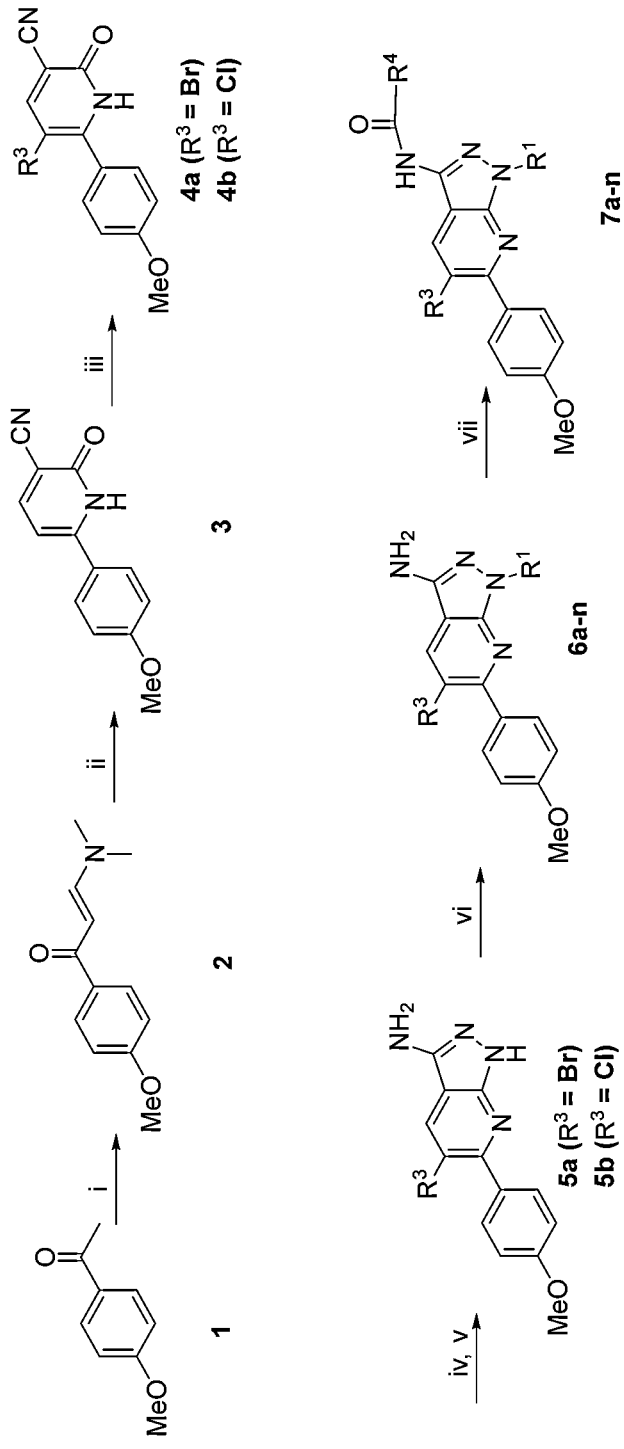
FIG. 3 includes an illustration of Scheme 1 for synthesizing the antiviral compounds.
Figure 3:
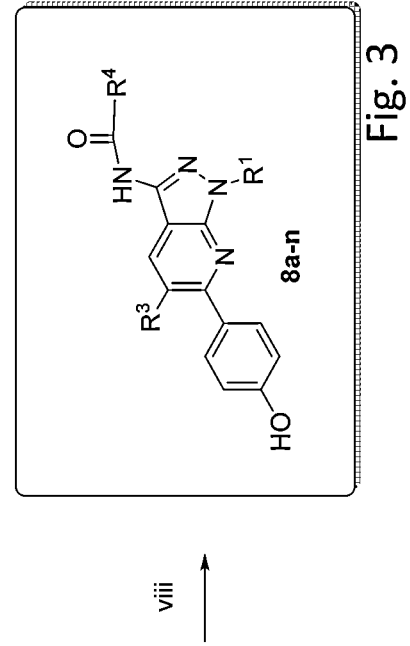

The antiviral compounds described herein can be synthesized as provided in Scheme 1 illustrated in FIG. 3. The reaction protocol of Scheme 1 is described as follows. The following reagents and conditions were utilized: (i) N,N-dimethylformamide dimethyl acetal, 110° C., 12 h; (ii) Cyanoacetamide, NaH, DMF, 110° C., 3 h; (iii) NBS or NCS, THF/MeOH (1:1), rt, 30 min; (iv) DMF, $POCl_3$, 110° C., 18 h; (v) $N_2H_2 \cdot H_2O$, EtOH, 85° C., 3 h; (vi) alkylhalide (s), NaH, DMF, 2 h; (vii) Nicotinoyl chloride, pyridine, 110° C.; or isothiazole-4-carboxylic acid, HATU, pyridine, 60° C., 8 h (viii) $BBr_3$, DCM, rt, 12 h.

Synthesis of (E)-3-(Dimethylamino)-1-(4-methoxyphenyl)prop-2-en-1-one (2). A mixture of 1-(4-methoxyphenyl) ethan-1-one (1) (3000 mg, 20.00 mmol) and N,N-dimethylformamide dimethyl acetal (4016 µL, 30.00 mmol) was stirred at 110° C. overnight. The reaction mixture was cooled to room temperature, then the solvent was removed under reduced pressure, and the resulting residue was purified by flash chromatography (10% MeOH/$CH_2Cl_2$) to afford compound 2a as a yellow solid (3600 mg, ~90%). $^1H$ NMR (500 MHz, Chloroform-d) δ 7.90 (d, J=8.8 Hz, 2H), 7.78 (d, J=12.4 Hz, 1H), 6.91 (d, J=8.7 Hz, 2H), 5.71 (d, J=12.3 Hz, 1H), 3.85 (s, 3H), 3.10-2.88 (m, 6H). MS (ESI-TOF) for $C_{12}H_{15}NO_2$ $[M+H]^+$ calculated 206.1176, found 206.1390.

Synthesis of 6-(4-methoxyphenyl)-2-oxo-1,2-dihydropyridine-3-carbonitrile (3). To a mixture of compound 2 (1800 mg, 8.77 mmol) and cyanoacetamide (886 mg, 10.53 mmol) in DMF (22 mL) was added NaH (60% dispersion in mineral oil, 1754 mg, 43.85 mmol). The mixture was stirred at 110° C. for 3 h. The reaction mixture was cooled to room temperature and the solvent was removed under reduced pressure. Water (50 mL) was added to the resulting residue, then the mixture was rendered acidic by the addition of acetic acid (5 mL) and stirred at 70° C. for 15 min. MeOH (12 mL) was added to the obtained mixture for suspension, and the deposited solid was washed with ethyl acetate (8.8 mL) and then dried under reduced pressure to yield compound 3 as a yellow solid, which was used in next step without further purification.

Syntheses of 5-Bromo-6-(4-methoxyphenyl)-2-oxo-1,2-dihydropyridine-3-carbonitrile (4a) and 5-Chloro-6-(4-methoxyphenyl)-2-oxo-1,2-dihydropyridine-3-carbonitrile (4b). To a suspension of compound 3 in THF/MeOH (48 mL, 1:1) was added either N-bromosuccinimide (1760 mg, 10.00 mmol), or N-chlorosuccinimide (1330 mg, 10.00 mmol). The mixture was stirred at room temperature for 30 min, and then the solvent was removed under reduced pressure. Water/hexane/EtOAc (72 mL, 1:1:1) was added to the crude material for suspension, and the deposited solid was washed with hexane (96 mL) and then dried under reduced pressure to yield compounds 4a and 4b as yellow solids. MS (ESI-TOF) for 4a $C_{13}H_9BrN_2O_2$ $[M+H]^+$ calculated 304.9920, found 304.9954. MS (ESI-TOF) for 4b $C_{13}H_9ClN_2O_2$ $[M+H]^+$ calculated 261.0425 found 261.0448.

Syntheses of 5-Bromo-6-(4-methoxyphenyl)-1H-pyrazolo[3,4-b]pyridine-3-amine (5a), and 5-Chloro-6-(4-methoxyphenyl)-1H-pyrazolo[3,4-b]pyridine-3-amine (5b). To a suspension of compound 4a (2650 mg, 8.68 mmol) or 4b (8 mmol) in $POCl_3$ (42 mL) was added DMF (1414 µL, 18.33 mmol). The mixture was stirred at 110° C. for 18 h. The reaction mixture was cooled to room temperature and the solvent was removed under reduced pressure. EtOAc (500 mL) was added to the crude material and the obtained mixture was poured into ice water (300 mL). The organic layer was washed with water (2×300 mL) and concentrated under reduced pressure, and the resultant residue was purified by flash chromatography (100% $CH_2Cl_2$) to afford the corresponding derivatives as colored (yellow/orange) solids which were used in next step without further purification. To a solution of hydrazine monohydrate (449 µL, 18.54 mmol) in EtOH (30 mL) were added the aforementioned 2-chloropyridine derivatives. The mixture was stirred at 85° C. for 3 hours. The reaction mixture was cooled to room temperature with the formation of solid. The formed solid was filtered and dried under reduced pressure to give compound 5a as a yellow solid (923 mg, 33% based on 4a). $^1H$ NMR (500 MHz, DMSO-d) for 5a: δ 12.11 (s, 1H), 8.50 (s, 1H), 7.58 (d, J=8.8 Hz, 2H), 7.02 (d, J=8.8 Hz, 2H), 5.68 (s, 2H), 3.82 (s, 3H). MS (ESI-TOF) for $C_{13}H_{11}BrN_4O$ $[M+H]^+$ calculated 319.0189; found 319.0233. MS (ESI-TOF) for $C_{13}H_{11}ClN_4O$ $[M+H]^+$ calculated 275.0694; found 275.0712.

General procedure for the syntheses of 5-halo-1-alkyl-6-(4-methoxyphenyl)-1H-pyrazolo[3,4-b]pyridine-3-amine (6a-n). To a solution of compound 5a (96 mg, 0.30 mmol) or 5b (0.3 mmol) an alkyl halide having the structure of $R^1$ in DMF (1.2 mL) cooled to 0° C. was added NaH (60% dispersion in mineral oil, 15 mg, 0.36 mmol). The resulting mixture was stirred for 30 min and then treated with appropriate haloalkanes (~0.35 mmol). The mixture was stirred at room temperature overnight, diluted with water (50 mL) and then extracted with EtOAc (3×50 mL). The combined organic layer was concentrated under reduced pressure, and the resulting residue was purified by flash chromatography (5% MeOH/$CH_2Cl_2$) to afford 6a (congeners) and 6b (congeners) as colored solids. MS (ESI-TOF) for the appropriate $M+H^+$ species were verified to be within 25 ppm of the calculated masses.

General procedure for the syntheses of N-(5-halo-6-(4-methoxyphenyl)-1-alkyl-1H-pyrazolo[3,4-b]pyridin-3-yl) nicotinamide, or N-(5-halo-6-(4-methoxyphenyl)-1-alkyl-1H-pyrazolo[3,4-b]pyridin-3-yl) isothiazole-4-carboxamide (7a-n). The syntheses of N-(5-halo-6-(4-methoxyphenyl)-1- alkyl-1H-pyrazolo[3,4-b]pyridin-3-yl)nicotinamide analogues were effected by direct coupling of nicotinyl chloride to the precursors 6a-n. To a solution of compound 6a-n (0.10 mmol) in pyridine (2 mL) was added either nicotinoyl chloride hydrochloride (0.15 mmol) and was stirred at 110° C. overnight. The reaction mixture was cooled to room temperature, then the solvent was removed under reduced pressure, and the resulting residue was purified by flash chromatography (10% MeOH/CH$_2$Cl$_2$ to afford the corresponding compounds nicotinamide derivatives as solids. MS (ESI-TOF) for the appropriate M+H$^+$ species were verified to be within 25 ppm of the calculated masses. The syntheses of N-(5-halo-6-(4-methoxyphenyl)-1-alkyl-1H-pyrazolo[3,4-b]pyridin-3-yl) isothiazole-4-carboxamide analogues were carried out by HATU (2-(3H-[1,2,3]triazolo[4,5-b]pyridin-3-yl)-1,1,3,3-tetramethylisouronium)-mediated coupling of isothiazole-4-carboxylic acid to precursors 6a-n. 1 equivalent of 6a-n, 1.2 equivalents of isothiazole-4-carboxylic acid, and 1.2 equivalents of HATU were dissolved in pyridine (4 ml), and stirred at 60° C. for up to 8 hours. The reaction mixture was cooled to room temperature, then the solvent was removed under reduced pressure, and the resulting residue was purified by flash chromatography (10% MeOH/CH$_2$Cl$_2$ to afford the corresponding compounds isothiazole carboxamide derivatives as solids. MS (ESI-TOF) for the appropriate M+H$^+$ species were verified to be within 25 ppm of the calculated masses.

General procedure for the syntheses of N-(5-halo-6-(4-hydroxyphenyl)-1-alkyl-1H-pyrazolo[3,4-b]pyridin-3-yl) nicotinamide, or N-(5-halo-6-(4-hydroxyphenyl)-1-alkyl-1H-pyrazolo[3,4-b]pyridin-3-yl) isothiazole-4-carboxamide (8a-n). To a solution or suspension of compounds 7a-n in dichloromethane (10 mL) was added boron tribromide (in molar excess), and was stirred at 60° C. for four hours. The reaction mixture was cooled to room temperature, then the solvent was removed under reduced pressure, and the resulting residue was purified by flash chromatography to afford O-demethylated compounds 8a-n as solids. MS (ESI-TOF) for the appropriate M+H$^+$ species were verified to be within 25 ppm of the calculated masses.

Antiviral Prodrug Compounds

The antiviral prodrug compounds described herein can be synthesized as provided in Scheme 2 illustrated in FIG. 4. The reaction protocol of Scheme 2 is described as follows. The prodrugs are configured to be cleaved to leave the hydroxyl group at the R$^2$ substituent. The following reagents and conditions were utilized: Reagents and conditions: (i) Carbonyldiimidazole, pyridine (1 h), (ii) N1,N1-dimethylethane-1,2-diamine; (iii) 2,4,6-tripropyl-1,3,5,2,4,6-trioxatriphosphinane 2,4,6-trioxide [T3P], pyridine, (iv) reverse-phase (C18) HPLC purification; (v) Di-tert-butyl chloromethyl phosphate, NaH, KI, DMF, r.t, (vi) Trifluoroacetic acid, (vii) reverse-phase (C18) HPLC purification.

General procedure for the syntheses of phenolic carbamate prodrugs 9a-n. To a solution of compounds 8a-n in pyridine (5 mL) was first added 1.1 equivalents of carbonyl diimidazole and stirred at room temperature for 1 h. Then 1.1-1.3 equivalents of N$^1$,N$^1$-dimethylethane-1,2-diamine was added, and stirred for an additional three hours. The phenolic carbamate prodrugs were purified by reverse-phase (C$_{18}$) HPLC. MS (ESI-TOF) for the appropriate M+H$^+$ species were verified to be within 25 ppm of the calculated masses.

General procedure for the syntheses of Phenyl hydrogen propylphosphonate derivatives 10a-n. To a solution of compounds 8a-n in pyridine (5 mL) was added 1.3 equivalents of 2,4,6-tripropyl-1,3,5,2,4,6-trioxatriphosphinane 2,4,6-trioxide (T3P) and stirred at room temperature for 3 h. The monopropylphosphonate derivatives were purified by reverse-phase (C$_{18}$) HPLC. MS (ESI-TOF) for the appropriate M+H$^+$ [positive ion mode] (and M−H$^+$) [negative ion mode] species were verified to be within 25 ppm of the calculated masses.

General procedure for the syntheses of methylene phosphate prodrugs 11a-n. To a solution of compounds 8a-n in dimethylformamide (5 mL) was first added 2 equivalents of di-tert-butyl chloromethyl phosphate, approximately 1 equivalent of sodium hydride suspension in mineral oil, and 1 equivalent of potassium iodide, and stirred at room temperature for 1-2 h. Then an excess of neat trifluoroacetic acid was added, and stirred for an additional one hour. The methylene phosphate prodrugs were purified by reverse-phase (C$_{18}$) HPLC. MS (ESI-TOF) for the appropriate M+H$^+$ [positive ion mode] (and M−H$^+$) [negative ion mode] species were verified to be within 25 ppm of the calculated masses.

DEFINITIONS

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

By "substituted" as in "substituted alkyl," "substituted aryl," and the like, as alluded to in some of the definitions provided herein, is meant that in the alkyl, aryl, or other moiety, at least one hydrogen atom bound to a carbon (or other) atom is replaced with one or more non-hydrogen substituents.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, heteroatom-containing alkenyl, and heteroatom-containing aryl."

As used herein, "optionally substituted" indicates that a chemical structure may be optionally substituted with a substituent group, such as defined herein. That is, when a chemical structure includes an atom that is optionally substituted, the atom may or may not include the optional substituent group, and thereby the chemical structure may be considered to be substituted when having a substituent on the atom or unsubstituted when omitting a substituent from the atom. A substituted group, referred to as a "substituent" or "substituent group", can be coupled (e.g., covalently) to a previously unsubstituted parent structure, wherein one or more hydrogens atoms (or other substituent groups) on the parent structure have been independently replaced by one or more of the substituents. The substituent is a chemical moiety that is added to a base chemical structure, such as a chemical scaffold. As such, a substituted chemical structure may have one or more substituent groups on the parent structure, such as by each substituent group being coupled to an atom of the parent structure. The substituent groups that can be coupled to the parent structure can be any possible substituent group. In examples of the present technology, the substituent groups (e.g., R groups) can be independently selected from an alkyl, —O-alkyl (e.g. —OCH$_3$, —OC$_2$H$_5$, —OC$_3$H$_7$, —OC$_4$H$_9$, etc.), —S-alkyl (e.g., —SCH$_3$, —SC$_2$H$_5$, —SC$_3$H$_7$, —SC$_4$H$_9$, etc.), —NR'R", —OH, —SH, —CN, —NO$_2$, or a halogen, wherein R' and R" are independently H or an optionally substituted alkyl. Wherever a substituent is described as "optionally substituted," that substituent can also be optionally substituted with the above substituents.

The term amino refers to the overall charged or net uncharged chemical group, where the R group can be a substituent, such as the substituents described herein:

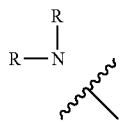

The term "alkyl" or "aliphatic" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl, and the like. Generally, although again not necessarily, alkyl groups herein contain 1 to about 18 carbon atoms, or 1 to about 12 carbon atoms. The term "lower alkyl" intends an alkyl group of 1 to 6 carbon atoms. Substituents identified as "C$_1$-C$_6$ alkyl" or "lower alkyl" contains 1 to 3 carbon atoms, and such substituents contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The terms "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein contain 2 to about 18 carbon atoms, or 2 to 12 carbon atoms. The term "lower alkenyl" intends an alkenyl group of 2 to 6 carbon atoms, and the specific term "cycloalkenyl" intends a cyclic alkenyl group, or having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein contain 2 to about 18 carbon atoms, or 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "C$_1$-C$_6$ alkoxy" or "lower alkoxy" herein contain 1 to 3 carbon atoms, and such substituents contain 1 or 2 carbon atoms (i.e., methoxy and ethoxy).

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Examples of aryl groups contain 5 to 20 carbon atoms, and aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aryloxy" as used herein refers to an aryl group bound through a single, terminal ether linkage, wherein "aryl" is as defined above. An "aryloxy" group may be represented as —O-aryl where aryl is as defined above. Examples of aryloxy groups contain 5 to 20 carbon atoms, and aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Examples of aralkyl groups contain 6 to 24 carbon atoms, and aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethyinaphthyl, 7-cyclooctylnaphthyl, 3-ethyl-cyclopenta-1,4-diene, and the like.

The term "cyclic" refers to alicyclic or aromatic substituents that may or may not be substituted and/or heteroatom containing, and that may be monocyclic, bicyclic, or polycyclic.

The terms "halo" and "halogen" are used in the conventional sense to refer to a chloro, bromo, and fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

The term "hydrocarbyl" refers to univalent hydrocarbyl radicals containing 1 to about 30 carbon atoms, or 1 to about 24 carbon atoms, or 1 to about 18 carbon atoms, or about 1 to 12 carbon atoms, including linear, branched, cyclic, saturated, and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

All other chemistry terms are defined as known in the art.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety.

The invention claimed is:
1. A compound selected from the group consisting of:
N-(5-bromo-6-(4-hydroxyphenyl)-1-(4-methylpentyl)-1H-pyrazolo[3,4-b]pyridin-3-yl)nicotinamide;
N-(5-bromo-1-hexyl-6-(4-hydroxyphenyl)-1H-pyrazolo[3,4-b]pyridin-3-yl)nicotinamide;
N-(5-bromo-6-(4-hydroxyphenyl)-1-(5-methylhexyl)-1H-pyrazolo[3,4-b]pyridin-3-yl)nicotinamide;
N-(5-bromo-1-(3-cyclopropylpropyl)-6-(4-hydroxyphenyl)-1H-pyrazolo[3,4-b]pyridin-3-yl)nicotinamide;
N-(5-bromo-1-heptyl-6-(4-hydroxyphenyl)-1H-pyrazolo[3,4-b]pyridin-3-yl)nicotinamide;
N-(5-bromo-1-(4-cyclopropylbutyl)-6-(4-hydroxyphenyl)-1H-pyrazolo[3,4-b]pyridin-3-yl)nicotinamide;
(4-(5-bromo-1-(4-methylpentyl)-3-(nicotinamido)-1H-pyrazolo[3,4-b]pyridin-6-yl)phenoxy)methyl dihydrogen phosphate;
4-(5-bromo-1-(4-methylpentyl)-3-(nicotinamido)-1H-pyrazolo[3,4-b]pyridin-6-yl)phenyl (2-(dimethylamino)ethyl)carbamate;
4-(5-bromo-1-(4-methylpentyl)-3-(nicotinamido)-1H-pyrazolo[3,4-b]pyridin-6-yl)phenyl hydrogen propylphosphonate;
4-(5-bromo-1-(4-methylpentyl)-3-(nicotinamido)-1H-pyrazolo[3,4-b]pyridin-6-yl)phenyl (3-(dimethylamino)propyl)carbamate;
(4-(5-bromo-1-(3-cyclopropylpropyl)-3-(nicotinamido)-1H-pyrazolo[3,4-b]pyridin-6-yl)phenoxy)methyl dihydrogen phosphate;
4-(5-bromo-1-(3-cyclopropylpropyl)-3-(nicotinamido)-1H-pyrazolo[3,4-b]pyridin-6-yl)phenyl (2-(dimethylamino)ethyl)carbamate;
4-(5-bromo-1-(3-cyclopropylpropyl)-3-(nicotinamido)-1H-pyrazolo[3,4-b]pyridin-6-yl)phenyl hydrogen propylphosphonate;
4-(5-bromo-1-(3-cyclopropylpropyl)-3-(nicotinamido)-1H-pyrazolo[3,4-b]pyridin-6-yl)phenyl (3-(dimethylamino)propyl)carbamate;
(4-(5-bromo-1-hexyl-3-(nicotinamido)-1H-pyrazolo[3,4-b]pyridin-6-yl)phenoxy)methyl dihydrogen phosphate;
4-(5-bromo-1-hexyl-3-(nicotinamido)-1H-pyrazolo[3,4-b]pyridin-6-yl)phenyl (2-(dimethylamino)ethyl)carbamate;
4-(5-bromo-1-hexyl-3-(nicotinamido)-1H-pyrazolo[3,4-b]pyridin-6-yl)phenyl hydrogen propylphosphonate;
4-(5-bromo-1-hexyl-3-(nicotinamido)-1H-pyrazolo[3,4-b]pyridin-6-yl)phenyl (3-(dimethylamino)propyl)carbamate;
(4-(5-bromo-1-(5-methylhexyl)-3-(nicotinamido)-1H-pyrazolo[3,4-b]pyridin-6-yl)phenoxy)methyl dihydrogen phosphate;
4-(5-bromo-1-(5-methylhexyl)-3-(nicotinamido)-1H-pyrazolo[3,4-b]pyridin-6-yl)phenyl (2-(dimethylamino)ethyl)carbamate;
4-(5-bromo-1-(5-methylhexyl)-3-(nicotinamido)-1H-pyrazolo[3,4-b]pyridin-6-yl)phenyl hydrogen propylphosphonate;
4-(5-bromo-1-(5-methylhexyl)-3-(nicotinamido)-1H-pyrazolo[3,4-b]pyridin-6-yl)phenyl (3-(dimethylamino)propyl)carbamate;
(4-(5-bromo-1-heptyl-3-(nicotinamido)-1H-pyrazolo[3,4-b]pyridin-6-yl)phenoxy)methyl dihydrogen phosphate;
4-(5-bromo-1-heptyl-3-(nicotinamido)-1H-pyrazolo[3,4-b]pyridin-6-yl)phenyl (2-(dimethylamino)ethyl)carbamate;
4-(5-bromo-1-heptyl-3-(nicotinamido)-1H-pyrazolo[3,4-b]pyridin-6-yl)phenyl hydrogen propylphosphonate;
4-(5-bromo-1-heptyl-3-(nicotinamido)-1H-pyrazolo[3,4-b]pyridin-6-yl)phenyl (3-(dimethylamino)propyl)carbamate;
(4-(5-bromo-1-(4-cyclopropylbutyl)-3-(nicotinamido)-1H-pyrazolo[3,4-b]pyridin-6-yl)phenoxy)methyl dihydrogen phosphate;
4-(5-bromo-1-(4-cyclopropylbutyl)-3-(nicotinamido)-1H-pyrazolo[3,4-b]pyridin-6-yl)phenyl (2-(dimethylamino)ethyl)carbamate;
4-(5-bromo-1-(4-cyclopropylbutyl)-3-(nicotinamido)-1H-pyrazolo[3,4-b]pyridin-6-yl)phenyl hydrogen propylphosphonate;
4-(5-bromo-1-(4-cyclopropylbutyl)-3-(nicotinamido)-1H-pyrazolo[3,4-b]pyridin-6-yl)phenyl (3-(dimethylamino)propyl)carbamate;
N-(5-chloro-6-(4-hydroxyphenyl)-1-(4-methylpentyl)-1H-pyrazolo[3,4-b]pyridin-3-yl)nicotinamide;
N-(5-chloro-1-hexyl-6-(4-hydroxyphenyl)-1H-pyrazolo[3,4-b]pyridin-3-yl)nicotinamide;
N-(5-chloro-6-(4-hydroxyphenyl)-1-(5-methylhexyl)-1H-pyrazolo[3,4-b]pyridin-3-yl)nicotinamide;
N-(5-chloro-1-(3-cyclopropylpropyl)-6-(4-hydroxyphenyl)-1H-pyrazolo[3,4-b]pyridin-3-yl)nicotinamide;
N-(5-chloro-1-heptyl-6-(4-hydroxyphenyl)-1H-pyrazolo[3,4-b]pyridin-3-yl)nicotinamide;

N-(5-chloro-1-(4-cyclopropylbutyl)-6-(4-hydroxyphenyl)-1H-pyrazolo[3,4-b]pyridin yl)nicotinamide;

(4-(5-chloro-1-(4-methylpentyl)-3-(nicotinamido)-1H-pyrazolo[3,4-b]pyridin yl)phenoxy)methyl dihydrogen phosphate;

4-(5-chloro-1-(4-methylpentyl)-3-(nicotinamido)-1H-pyrazolo[3,4-b]pyridin-6-yl)phenyl (2-(dimethylamino)ethyl)carbamate;

4-(5-chloro-1-(4-methylpentyl)-3-(nicotinamido)-1H-pyrazolo[3,4-b]pyridin-6-yl)phenyl hydrogen propylphosphonate;

4-(5-chloro-1-(4-methylpentyl)-3-(nicotinamido)-1H-pyrazolo[3,4-b]pyridin-6-yl)phenyl (3-(dimethylamino)propyl)carbamate;

(4-(5-chloro-1-(3-cyclopropylpropyl)-3-(nicotinamido)-1H-pyrazolo[3,4-b]pyridin-6-yl)phenoxy)methyl dihydrogen phosphate;

4-(5-chloro-1-(3-cyclopropylpropyl)-3-(nicotinamido)-1H-pyrazolo[3,4-b]pyridin-6-yl)phenyl (2-(dimethylamino)ethyl)carbamate;

4-(5-chloro-1-(3-cyclopropylpropyl)-3-(nicotinamido)-1H-pyrazolo[3,4-b]pyridin-6-yl)phenyl hydrogen propylphosphonate;

4-(5-chloro-1-(3-cyclopropylpropyl)-3-(nicotinamido)-1H-pyrazolo[3,4-b]pyridin-6-yl)phenyl (3-(dimethylamino)propyl)carbamate;

(4-(5-chloro-1-hexyl-3-(nicotinamido)-1H-pyrazolo[3,4-b]pyridin-6-yl)phenoxy)methyl dihydrogen phosphate;

4-(5-chloro-1-hexyl-3-(nicotinamido)-1H-pyrazolo[3,4-b]pyridin-6-yl)phenyl (2-(dimethylamino)ethyl)carbamate;

4-(5-chloro-1-hexyl-3-(nicotinamido)-1H-pyrazolo[3,4-b]pyridin-6-yl)phenyl hydrogen propylphosphonate;

4-(5-chloro-1-hexyl-3-(nicotinamido)-1H-pyrazolo[3,4-b]pyridin-6-yl)phenyl (3-(dimethylamino)propyl)carbamate;

(4-(5-chloro-1-(5-methylhexyl)-3-(nicotinamido)-1H-pyrazolo[3,4-b]pyridin yl)phenoxy)methyl dihydrogen phosphate;

4-(5-chloro-1-(5-methylhexyl)-3-(nicotinamido)-1H-pyrazolo[3,4-b]pyridin-6-yl)phenyl (2-(dimethylamino)ethyl)carbamate;

4-(5-chloro-1-(5-methylhexyl)-3-(nicotinamido)-1H-pyrazolo[3,4-b]pyridin-6-yl)phenyl hydrogen propylphosphonate;

4-(5-chloro-1-(5-methylhexyl)-3-(nicotinamido)-1H-pyrazolo[3,4-b]pyridin-6-yl)phenyl (3-(dimethylamino)propyl)carbamate;

(4-(5-chloro-1-heptyl-3-(nicotinamido)-1H-pyrazolo[3,4-b]pyridin-6-yl)phenoxy)methyl dihydrogen phosphate;

4-(5-chloro-1-heptyl-3-(nicotinamido)-1H-pyrazolo[3,4-b]pyridin-6-yl)phenyl (2-(dimethylamino)ethyl)carbamate;

4-(5-chloro-1-heptyl-3-(nicotinamido)-1H-pyrazolo[3,4-b]pyridin-6-yl)phenyl hydrogen propylphosphonate;

4-(5-chloro-1-heptyl-3-(nicotinamido)-1H-pyrazolo[3,4-b]pyridin-6-yl)phenyl (3-(dimethylamino)propyl)carbamate;

(4-(5-chloro-1-(4-cyclopropylbutyl)-3-(nicotinamido)-1H-pyrazolo[3,4-b]pyridin-6-yl)phenoxy)methyl dihydrogen phosphate;

4-(5-chloro-1-(4-cyclopropylbutyl)-3-(nicotinamido)-1H-pyrazolo[3,4-b]pyridin-6-yl)phenyl (2-(dimethylamino)ethyl)carbamate;

4-(5-chloro-1-(4-cyclopropylbutyl)-3-(nicotinamido)-1H-pyrazolo[3,4-b]pyridin-6-yl)phenyl hydrogen propylphosphonate; or 4-(5-chloro-1-(4-cyclopropylbutyl)-3-(nicotinamido)-1H-pyrazolo[3,4-b]pyridin-6-yl)phenyl (3-(dimethylamino)propyl)carbamate.

2. A compound selected from the group consisting of:

N-(5-bromo-6-(4-hydroxyphenyl)-1-(4-methylpentyl)-1H-pyrazolo[3,4-b]pyridin yl)isothiazole-4-carboxamide;

N-(5-bromo-1-hexyl-6-(4-hydroxyphenyl)-1H-pyrazolo[3,4-b]pyridin-3-yl)isothiazole carboxamide;

N-(5-bromo-6-(4-hydroxyphenyl)-1-(5-methylhexyl)-1H-pyrazolo[3,4-b]pyridin-3-yl)isothiazole-4-carboxamide;

N-(5-bromo-1-(3-cyclopropylpropyl)-6-(4-hydroxyphenyl)-1H-pyrazolo[3,4-b]pyridin-3-yl)isothiazole-4-carboxamide;

N-(5-bromo-1-heptyl-6-(4-hydroxyphenyl)-1H-pyrazolo[3,4-b]pyridin-3-yl)isothiazole-4-carboxamide;

N-(5-bromo-1-(4-cyclopropylbutyl)-6-(4-hydroxyphenyl)-1H-pyrazolo[3,4-b]pyridin-3-yl)isothiazole-4-carboxamide;

(4-(5-bromo-3-(isothiazole-4-carboxamido)-1-(4-methylpentyl)-1H-pyrazolo[3,4-b]pyridin-6-yl)phenoxy)methyl dihydrogen phosphate;

4-(5-bromo-3-(isothiazole-4-carboxamido)-1-(4-methylpentyl)-1H-pyrazolo[3,4-b]pyridin-6-yl)phenyl (2-(dimethylamino)ethyl)carbamate;

4-(5-bromo-3-(isothiazole-4-carboxamido)-1-(4-methylpentyl)-1H-pyrazolo[3,4-b]pyridin-6-yl)phenyl hydrogen propylphosphonate;

4-(5-bromo-3-(isothiazole-4-carboxamido)-1-(4-methylpentyl)-1H-pyrazolo[3,4-b]pyridin-6-yl)phenyl (3-(dimethylamino)propyl)carbamate;

(4-(5-bromo-1-hexyl-3-(isothiazole-4-carboxamido)-1H-pyrazolo[3,4-b]pyridin-6-yl)phenoxy)methyl dihydrogen phosphate;

4-(5-bromo-1-hexyl-3-(isothiazole-4-carboxamido)-1H-pyrazolo[3,4-b]pyridin-6-yl)phenyl (2-(dimethylamino)ethyl)carbamate;

4-(5-bromo-1-hexyl-3-(isothiazole-4-carboxamido)-1H-pyrazolo[3,4-b]pyridin-6-yl)phenyl hydrogen propylphosphonate;

4-(5-bromo-1-hexyl-3-(isothiazole-4-carboxamido)-1H-pyrazolo[3,4-b]pyridin yl)phenyl (3-(dimethylamino)propyl)carbamate;

(4-(5-bromo-3-(isothiazole-4-carboxamido)-1-(5-methylhexyl)-1H-pyrazolo[3,4-b]pyridin-6-yl)phenoxy)methyl dihydrogen phosphate;

4-(5-bromo-3-(isothiazole-4-carboxamido)-1-(5-methylhexyl)-1H-pyrazolo[3,4-b]pyridin-6-yl)phenyl (2-(dimethylamino)ethyl)carbamate;

4-(5-bromo-3-(isothiazole-4-carboxamido)-1-(5-methylhexyl)-1H-pyrazolo[3,4-b]pyridin-6-yl)phenyl hydrogen propylphosphonate;

4-(5-bromo-3-(isothiazole-4-carboxamido)-1-(5-methylhexyl)-1H-pyrazolo[3,4-b]pyridin-6-yl)phenyl (3-(dimethylamino)propyl)carbamate;

(4-(5-bromo-1-heptyl-3-(isothiazole-4-carboxamido)-1H-pyrazolo[3,4-b]pyridin-6-yl)phenoxy)methyl dihydrogen phosphate;

4-(5-bromo-1-heptyl-3-(isothiazole-4-carboxamido)-1H-pyrazolo[3,4-b]pyridin-6-yl)phenyl (2-(dimethylamino)ethyl)carbamate;

4-(5-bromo-1-heptyl-3-(isothiazole-4-carboxamido)-1H-pyrazolo[3,4-b]pyridin-6-yl)phenyl hydrogen propylphosphonate;

4-(5-bromo-1-heptyl-3-(isothiazole-4-carboxamido)-1H-pyrazolo[3,4-b]pyridin-6-yl)phenyl (3-(dimethylamino)propyl)carbamate;

(4-(5-bromo-1-(3-cyclopropylpropyl)-3-(isothiazole-4-carboxamido)-1H-pyrazolo[3,4-b]pyridin-6-yl)phenoxy)methyl dihydrogen phosphate;

4-(5-bromo-1-(3-cyclopropylpropyl)-3-(isothiazole-4-carboxamido)-1H-pyrazolo[3,4-b]pyridin-6-yl)phenyl (2-(dimethylamino)ethyl)carbamate;

4-(5-bromo-1-(3-cyclopropylpropyl)-3-(isothiazole-4-carboxamido)-1H-pyrazolo[3,4-b]pyridin-6-yl)phenyl hydrogen propylphosphonate;

4-(5-bromo-1-(3-cyclopropylpropyl)-3-(isothiazole-4-carboxamido)-1H-pyrazolo[3,4-b]pyridin-6-yl)phenyl (3-(dimethylamino)propyl)carbamate;

(4-(5-bromo-1-(4-cyclopropylbutyl)-3-(isothiazole-4-carboxamido)-1H-pyrazolo[3,4-b]pyridin-6-yl)phenoxy)methyl dihydrogen phosphate;

4-(5-bromo-1-(4-cyclopropylbutyl)-3-(isothiazole-4-carboxamido)-1H-pyrazolo[3,4-b]pyridin-6-yl)phenyl (2-(dimethylamino)ethyl)carbamate;

4-(5-bromo-1-(4-cyclopropylbutyl)-3-(isothiazole-4-carboxamido)-1H-pyrazolo[3,4-b]pyridin-6-yl)phenyl hydrogen propylphosphonate;

4-(5-bromo-1-(4-cyclopropylbutyl)-3-(isothiazole-4-carboxamido)-1H-pyrazolo[3,4-b]pyridin-6-yl)phenyl (3-(dimethylamino)propyl)carbamate;

N-(5-chloro-6-(4-hydroxyphenyl)-1-(4-methylpentyl)-1H-pyrazolo[3,4-b]pyridin-3-yl)isothiazole-4-carboxamide;

N-(5-chloro-1-hexyl-6-(4-hydroxyphenyl)-1H-pyrazolo[3,4-b]pyridin-3-yl)isothiazole-4-carboxamide;

N-(5-chloro-6-(4-hydroxyphenyl)-1-(5-methylhexyl)-1H-pyrazolo[3,4-b]pyridin-3-yl)isothiazole-4-carboxamide;

N-(5-chloro-1-(3-cyclopropylpropyl)-6-(4-hydroxyphenyl)-1H-pyrazolo[3,4-b]pyridin-3-yl)isothiazole-4-carboxamide;

N-(5-chloro-1-heptyl-6-(4-hydroxyphenyl)-1H-pyrazolo[3,4-b]pyridin-3-yl)isothiazole-4-carboxamide;

N-(5-chloro-1-(4-cyclopropylbutyl)-6-(4-hydroxyphenyl)-1H-pyrazolo[3,4-b]pyridin-3-yl)isothiazole-4-carboxamide;

(4-(5-chloro-3-(isothiazole-4-carboxamido)-1-(4-methylpentyl)-1H-pyrazolo[3,4-b]pyridin-6-yl)phenoxy)methyl dihydrogen phosphate;

4-(5-chloro-3-(isothiazole-4-carboxamido)-1-(4-methylpentyl)-1H-pyrazolo[3,4-b]pyridin-6-yl)phenyl (2-(dimethylamino)ethyl)carbamate;

4-(5-chloro-3-(isothiazole-4-carboxamido)-1-(4-methylpentyl)-1H-pyrazolo[3,4-b]pyridin-6-yl)phenyl hydrogen propylphosphonate;

4-(5-chloro-3-(isothiazole-4-carboxamido)-1-(4-methylpentyl)-1H-pyrazolo[3,4-b]pyridin-6-yl)phenyl (3-(dimethylamino)propyl)carbamate;

(4-(5-chloro-1-hexyl-3-(isothiazole-4-carboxamido)-1H-pyrazolo[3,4-b]pyridin yl)phenoxy)methyl dihydrogen phosphate;

4-(5-chloro-1-hexyl-3-(isothiazole-4-carboxamido)-1H-pyrazolo[3,4-b]pyridin-6-yl)phenyl (2-(dimethylamino)ethyl)carbamate;

4-(5-chloro-1-hexyl-3-(isothiazole-4-carboxamido)-1H-pyrazolo[3,4-b]pyridin-6-yl)phenyl hydrogen propylphosphonate;

4-(5-chloro-1-hexyl-3-(isothiazole-4-carboxamido)-1H-pyrazolo[3,4-b]pyridin-6-yl)phenyl (3-(dimethylamino)propyl)carbamate;

(4-(5-chloro-3-(isothiazole-4-carboxamido)-1-(5-methylhexyl)-1H-pyrazolo[3,4-b]pyridin-6-yl)phenoxy)methyl dihydrogen phosphate;

4-(5-chloro-3-(isothiazole-4-carboxamido)-1-(5-methylhexyl)-1H-pyrazolo[3,4-b]pyridin-6-yl)phenyl (2-(dimethylamino)ethyl)carbamate;

4-(5-chloro-3-(isothiazole-4-carboxamido)-1-(5-methylhexyl)-1H-pyrazolo[3,4-b]pyridin-6-yl)phenyl hydrogen propylphosphonate;

4-(5-chloro-3-(isothiazole-4-carboxamido)-1-(5-methylhexyl)-1H-pyrazolo[3,4-b]pyridin-6-yl)phenyl (3-(dimethylamino)propyl)carbamate;

(4-(5-chloro-1-heptyl-3-(isothiazole-4-carboxamido)-1H-pyrazolo[3,4-b]pyridin-6-yl)phenoxy)methyl dihydrogen phosphate;

4-(5-chloro-1-heptyl-3-(isothiazole-4-carboxamido)-1H-pyrazolo[3,4-b]pyridin-6-yl)phenyl (2-(dimethylamino)ethyl)carbamate;

4-(5-chloro-1-heptyl-3-(isothiazole-4-carboxamido)-1H-pyrazolo[3,4-b]pyridin-6-yl)phenyl hydrogen propylphosphonate;

4-(5-chloro-1-heptyl-3-(isothiazole-4-carboxamido)-1H-pyrazolo[3,4-b]pyridin-6-yl)phenyl (3-(dimethylamino)propyl)carbamate;

(4-(5-chloro-1-(3-cyclopropylpropyl)-3-(isothiazole-4-carboxamido)-1H-pyrazolo[3,4-b]pyridin-6-yl)phenoxy)methyl dihydrogen phosphate;

4-(5-chloro-1-(3-cyclopropylpropyl)-3-(isothiazole-4-carboxamido)-1H-pyrazolo[3,4-b]pyridin-6-yl)phenyl (2-(dimethylamino)ethyl)carbamate;

4-(5-chloro-1-(3-cyclopropylpropyl)-3-(isothiazole-4-carboxamido)-1H-pyrazolo[3,4-b]pyridin-6-yl)phenyl hydrogen propylphosphonate;

4-(5-chloro-1-(3-cyclopropylpropyl)-3-(isothiazole-4-carboxamido)-1H-pyrazolo[3,4-b]pyridin-6-yl)phenyl (3-(dimethylamino)propyl)carbamate;

(4-(5-chloro-1-(4-cyclopropylbutyl)-3-(isothiazole-4-carboxamido)-1H-pyrazolo[3,4-b]pyridin-6-yl)phenoxy)methyl dihydrogen phosphate;

4-(5-chloro-1-(4-cyclopropylbutyl)-3-(isothiazole-4-carboxamido)-1H-pyrazolo[3,4-b]pyridin-6-yl)phenyl (2-(dimethylamino)ethyl)carbamate;

4-(5-chloro-1-(4-cyclopropylbutyl)-3-(isothiazole-4-carboxamido)-1H-pyrazolo[3,4-b]pyridin-6-yl)phenyl hydrogen propylphosphonate; or 4-(5-chloro-1-(4-cyclopropylbutyl)-3-(isothiazole-4-carboxamido)-1H-pyrazolo[3,4-b]pyridin-6-yl)phenyl (3-(dimethylamino)propyl)carbamate.

3. A pharmaceutical composition comprising:
the compound of claim 1; and
a pharmaceutically acceptable carrier.

4. A method of providing an antiviral therapy comprising:
administering the compound of claim 1 to a subject having or suspected of having or exposed to a virus.

5. The method of 4, wherein the compound is administered to the subject in an effective amount for treating, inhibiting, preventing, or slowing progression of the virus.

6. The method of claim 4, wherein the virus is selected from: Semliki Forest virus complex, Venezuelan equine encephalitis complex, Eastern equine encephalitis complex, Western equine encephalitis complex, and flaviviruses, or combinations thereof.

7. A pharmaceutical composition comprising:
the compound of claim 2; and
a pharmaceutically acceptable carrier.

8. A method of providing an antiviral therapy comprising: administering the compound of claim 2 to a subject having or suspected of having or exposed to a virus.

9. The method of 8, wherein the compound is administered to the subject in an effective amount for treating, inhibiting, preventing, or slowing progression of the virus.

10. The method of claim 8, wherein the virus is selected from:
Semliki Forest virus complex, Venezuelan equine encephalitis complex, Eastern equine encephalitis complex, Western equine encephalitis complex, and flaviviruses, or combinations thereof.

11. A compound selected from the group consisting of:
(4-(5-bromo-1-(4-methylpentyl)-3-(nicotinamido)-1H-pyrazolo[3,4-b]pyridin-6-yl)phenoxy)methyl dihydrogen phosphate;
4-(5-bromo-1-(4-methylpentyl)-3-(nicotinamido)-1H-pyrazolo[3,4-b]pyridin-6-yl)phenyl (2-(dimethylamino)ethyl)carbamate;
4-(5-bromo-1-(4-methylpentyl)-3-(nicotinamido)-1H-pyrazolo[3,4-b]pyridin-6-yl)phenyl hydrogen propylphosphonate;
4-(5-bromo-1-(4-methylpentyl)-3-(nicotinamido)-1H-pyrazolo[3,4-b]pyridin-6-yl)phenyl (3-(dimethylamino)propyl)carbamate;
N-(5-bromo-6-(4-hydroxyphenyl)-1-(4-methylpentyl)-1H-pyrazolo[3,4-b]pyridin-3-yl)nicotinamide;
(4-(5-bromo-1-hexyl-3-(nicotinamido)-1H-pyrazolo[3,4-b]pyridin-6-yl)phenoxy)methyl dihydrogen phosphate;
4-(5-bromo-1-hexyl-3-(nicotinamido)-1H-pyrazolo[3,4-b]pyridin-6-yl)phenyl (2-(dimethylamino)ethyl)carbamate;
4-(5-bromo-1-hexyl-3-(nicotinamido)-1H-pyrazolo[3,4-b]pyridin-6-yl)phenyl hydrogen propylphosphonate;
4-(5-bromo-1-hexyl-3-(nicotinamido)-1H-pyrazolo[3,4-b]pyridin-6-yl)phenyl (3-(dimethylamino)propyl)carbamate; or
N-(5-bromo-1-hexyl-6-(4-hydroxyphenyl)-1H-pyrazolo[3,4-b]pyridin-3-yl)nicotinamide.

12. The compound of claim 11, wherein the compound is selected from the group consisting of:
(4-(5-bromo-1-(4-methylpentyl)-3-(nicotinamido)-1H-pyrazolo[3,4-b]pyridin-6-yl)phenoxy)methyl dihydrogen phosphate;
4-(5-bromo-1-(4-methylpentyl)-3-(nicotinamido)-1H-pyrazolo[3,4-b]pyridin-6-yl)phenyl (2-(dimethylamino)ethyl)carbamate;
4-(5-bromo-1-(4-methylpentyl)-3-(nicotinamido)-1H-pyrazolo[3,4-b]pyridin-6-yl)phenyl hydrogen propylphosphonate;
4-(5-bromo-1-(4-methylpentyl)-3-(nicotinamido)-1H-pyrazolo[3,4-b]pyridin-6-yl)phenyl (3-(dimethylamino)propyl)carbamate; or
N-(5-bromo-6-(4-hydroxyphenyl)-1-(4-methylpentyl)-1H-pyrazolo[3,4-b]pyridin-3-yl)nicotinamide.

13. The compound of claim 11, wherein the compound is selected from the group consisting of:
(4-(5-bromo-1-(4-methylpentyl)-3-(nicotinamido)-1H-pyrazolo[3,4-b]pyridin-6-yl)phenoxy)methyl dihydrogen phosphate;
4-(5-bromo-1-(4-methylpentyl)-3-(nicotinamido)-1H-pyrazolo[3,4-b]pyridin-6-yl)phenyl (2-(dimethylamino)ethyl)carbamate; or
N-(5-bromo-6-(4-hydroxyphenyl)-1-(4-methylpentyl)-1H-pyrazolo[3,4-b]pyridin yl)nicotinamide.

14. The compound of claim 11, wherein the compound is selected from the group consisting of:
(4-(5-bromo-1-hexyl-3-(nicotinamido)-1H-pyrazolo[3,4-b]pyridin-6-yl)phenoxy)methyl dihydrogen phosphate;
4-(5-bromo-1-hexyl-3-(nicotinamido)-1H-pyrazolo[3,4-b]pyridin-6-yl)phenyl (2-(dimethylamino)ethyl)carbamate;
4-(5-bromo-1-hexyl-3-(nicotinamido)-1H-pyrazolo[3,4-b]pyridin-6-yl)phenyl hydrogen propylphosphonate;
4-(5-bromo-1-hexyl-3-(nicotinamido)-1H-pyrazolo[3,4-b]pyridin-6-yl)phenyl (3-(dimethylamino)propyl)carbamate; or
N-(5-bromo-1-hexyl-6-(4-hydroxyphenyl)-1H-pyrazolo[3,4-b]pyridin-3-yl)nicotinamide.

15. The compound of claim 11, wherein the compound is selected from the group consisting of:
(4-(5-bromo-1-hexyl-3-(nicotinamido)-1H-pyrazolo[3,4-b]pyridin-6-yl)phenoxy)methyl dihydrogen phosphate;
4-(5-bromo-1-hexyl-3-(nicotinamido)-1H-pyrazolo[3,4-b]pyridin-6-yl)phenyl (2-(dimethylamino)ethyl)carbamate; or
N-(5-bromo-1-hexyl-6-(4-hydroxyphenyl)-1H-pyrazolo[3,4-b]pyridin-3-yl)nicotinamide.

16. The compound of claim 11, wherein the compound is selected from the group consisting of:
(4-(5-bromo-1-(4-methylpentyl)-3-(nicotinamido)-1H-pyrazolo[3,4-b]pyridin yl)phenoxy)methyl dihydrogen phosphate; or
4-(5-bromo-1-(4-methylpentyl)-3-(nicotinamido)-1H-pyrazolo[3,4-b]pyridin-6-yl)phenyl (2-(dimethylamino)ethyl)carbamate.

17. The compound of claim 11, wherein the compound is N-(5-bromo-6-(4-hydroxyphenyl)-1-(4-methylpentyl)-1H-pyrazolo[3,4-b]pyridin-3-yl)nicotinamide.

18. The compound of claim 11, wherein the compound is selected from the group consisting of:
(4-(5-bromo-1-hexyl-3-(nicotinamido)-1H-pyrazolo[3,4-b]pyridin-6-yl)phenoxy)methyl dihydrogen phosphate; or
4-(5-bromo-1-hexyl-3-(nicotinamido)-1H-pyrazolo[3,4-b]pyridin-6-yl)phenyl (2-(dimethylamino)ethyl)carbamate.

19. The compound of claim 11, wherein the compound is N-(5-bromo-1-hexyl-6-(4-hydroxyphenyl)-1H-pyrazolo[3,4-b]pyridin-3-yl)nicotinamide.

* * * * *